United States Patent
Hishikawa

(10) Patent No.: US 6,811,139 B2
(45) Date of Patent: Nov. 2, 2004

(54) CONNECTOR

(75) Inventor: Yoshinori Hishikawa, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 174 days.

(21) Appl. No.: 10/168,107

(22) PCT Filed: Dec. 18, 2000

(86) PCT No.: PCT/JP00/08964

§ 371 (c)(1),
(2), (4) Date: Oct. 25, 2002

(87) PCT Pub. No.: WO01/43813

PCT Pub. Date: May 21, 2001

(65) Prior Publication Data

US 2003/0066980 A1 Apr. 10, 2003

(51) Int. Cl.[7] ............... F16K 51/00; F16L 29/00; F16L 37/28
(52) U.S. Cl. ............. 251/149.1; 604/256; 604/905
(58) Field of Search .................. 251/149, 149.1, 251/149.3, 149.8, 149.9; 604/246, 249, 256, 537, 538, 905

(56) References Cited

U.S. PATENT DOCUMENTS

| | | | |
|---|---|---|---|
| 3,788,598 A | 1/1974 | German et al. | |
| 4,842,591 A | 6/1989 | Luther | |
| 5,676,346 A | 10/1997 | Leinsing | |
| 5,699,821 A | * 12/1997 | Paradis | ............ 137/1 |
| 6,089,541 A | * 7/2000 | Weinheimer et al. | .... 251/149.6 |
| 6,113,068 A | * 9/2000 | Ryan | ............ 251/149.4 |

FOREIGN PATENT DOCUMENTS

| | | |
|---|---|---|
| DE | 196 39 870 C1 | 12/1997 |
| JP | 184300/1982 | 6/1984 |
| JP | 138265/1983 | 3/1985 |
| JP | 9-108361 A | 4/1987 |
| JP | 86055/1986 | 12/1987 |
| JP | 2-104372 A | 4/1990 |
| JP | 2000-14797 A | 1/2000 |

* cited by examiner

*Primary Examiner*—Edward K. Look
*Assistant Examiner*—John K. Fristoe, Jr.
(74) *Attorney, Agent, or Firm*—Burns, Doane, Swecker, Mathis, L.L.P.

(57) ABSTRACT

A connector is provided which has a fluid passage whose volume does not substantially vary with the opening/closing of a valve disc. The connector includes a substantially cylindrical connector main body, a valve disc made of elastic material and disposed at one of the opening ends of the connector main body, and a substantially cylindrical connecting member disposed on the outer periphery of the connector main body on the side of the valve disc and coaxially with the connector main body to be movable in an axial direction of the connector main body.

20 Claims, 19 Drawing Sheets

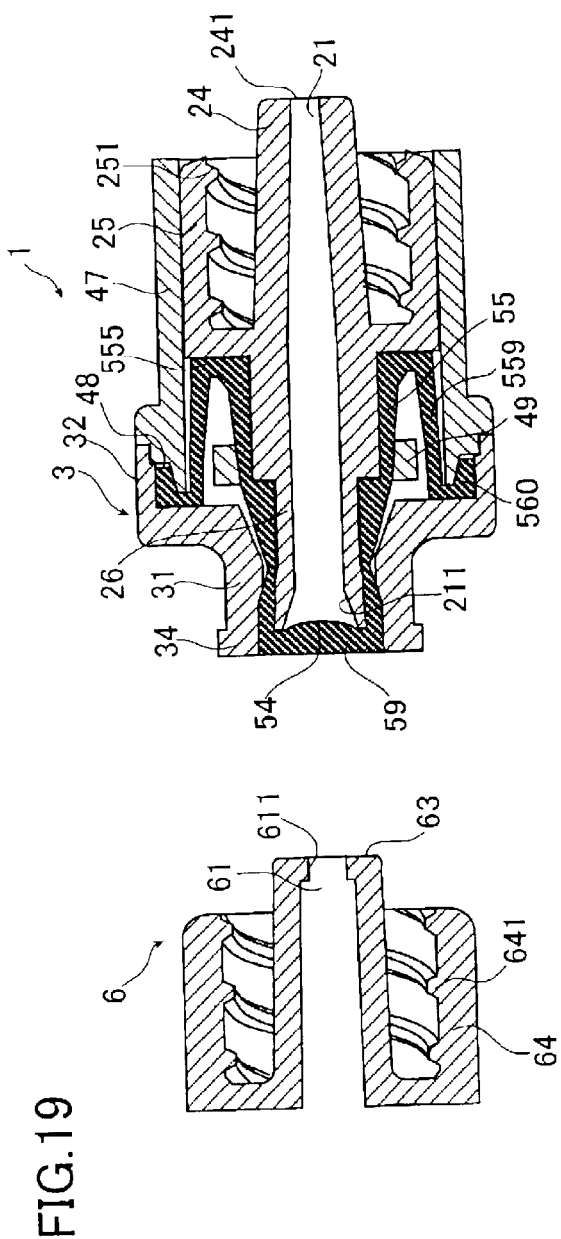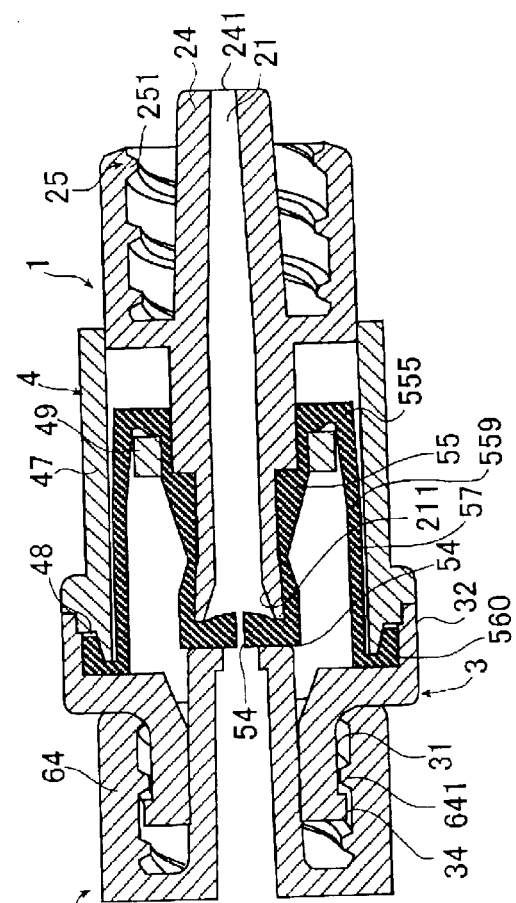
FIG.19
FIG.20

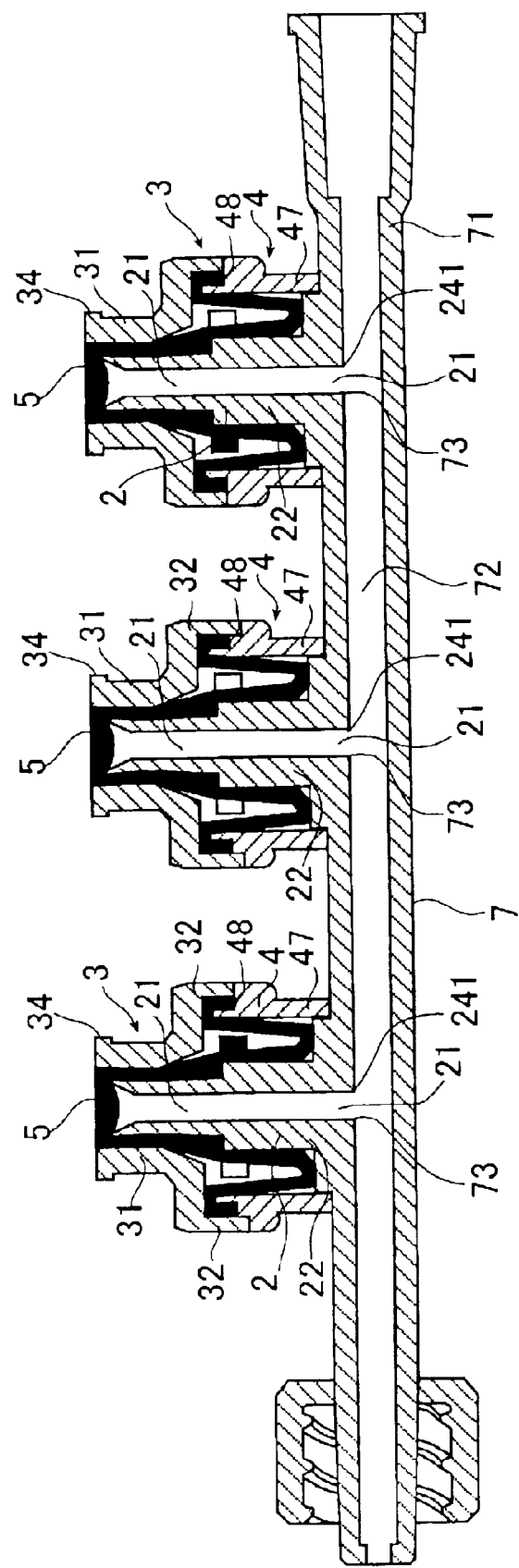

CONNECTOR

TECHNICAL FIELD

The present invention relates to a connector for connecting a duct used in, for example, various medical equipment, fluid infusion containers, and fluid feeding equipment.

BACKGROUND ART

A connector for connecting a duct is provided with a housing and a valve disc made of elastic material and connected to a connecting port of this housing, and is structured so as to be positively connected to the duct by this valve disc. The fluid flowing through the duct is fed to the interior of the connector.

The connector of such type is conventionally known from one disclosed in, for example, JP 9-108361 A.

This connector is provided with the valve disc having a bellows-like section (bellows section). When a duct is connected to the connector, the bellows section of the valve disc shrinks by means of the duct so that an end surface of the valve disc is pushed against the duct. Thus, the leakage of liquid from a slit of the valve disc is prevented.

However, in the conventional connector, when the duct is connected to the connector, the valve disc shrinks so that a flow path volume of the interior of the valve disc, i.e., the flow path volume of the connector is decreased in comparison with the case where the valve disc is closed, which causes various problems.

For example, in the case where the connector is connected to a catheter disposed in a blood vessel and used, the duct is connected to the connector, and an anticoagulant agent is infused into the catheter from the duct through the connector. Thereafter, when the duct is removed away from the connector, the bellows section of the valve disc is extended so that the flow path volume of the connector is increased. At this time, the blood is sucked into the catheter by a negative pressure.

Thus, the blood is coagulated to cause thrombi within the catheter so that the catheter is clogged and can not be used. For this reason, the catheter has to be removed. The number of operations is increased to impose a load to the patient.

DISCLOSURE OF THE INVENTION

An object of the present invention is to provide a connector having a fluid passage whose volume does not substantially vary with the opening/closing of a valve disc.

Such an object is attained by the present inventions (1) to (17) described below.

(1) A connector including: a substantially cylindrical connector main body having a fluid passage in its interior and opened at both ends; a valve disc disposed at one of opening ends of the connector main body and made of elastic material for opening the fluid passage within the connector main body upon the connection with a duct to be connected to the connector main body and closing upon the non-connection; and a substantially cylindrical connecting member disposed on the outer periphery of the connector main body on a side of the valve disc and coaxially with the connector main body to be movable in an axial direction of the connector main body.

(2) The connector according to the above-described item (1), in which the valve disc is opened by a pressure from the duct without the duct passing through the interior of the valve disc.

Normally, the duct has a taper outer peripheral surface that decreases gradually in a distal end direction. Also, the duct has a lure lock, and a flange is formed at an end section of the connecting member of the connector. If these are engaged with each other, it is possible to hold the connection more stably.

(3) The connector according to the above-described item (1) or (2), in which the duct is fit to an opening of the connecting member to thereby connect and hold the duct.

(4) The connector according to any one of the above-described items (1) to (3), further including biasing means for biasing the connecting member toward the connector main body.

(5) The connector according to the above-described item (4), in which the biasing means is composed of a spiral spring, a bellows spring or a stepwise spring.

(6) The connector according to any one of the above-described items (1) to (5), further including a position regulating means for regulating a position of the connecting member so as to expose a part of the valve disc in the vicinity of the connecting port at the time when the duct is not connected to the connecting port.

(7) The connector according to any one of the above-described items (1) to (6), in which the valve disc has a pressed section in which a slit section that is opened due to reception of the pressure from the duct is formed.

(8) In the connector according to the above-described item (7), in which the pressed section has a curved convex surface on at least one of a surface on a side with which a distal end surface of the duct contacts and a surface on its back side.

(9) The connector according to the above-described item (7), in which the pressed section has a curved concave surface on a surface of a side with which a distal end surface of the duct contacts.

(10) The connector according to any one of the above-described items (7) to (9), in which the surface on the back side on the side, with which the distal end surface of the duct contacts, of the pressed section is flat.

(11) The connector according to the above-described item (9), in which the pressed section has a curved convex surface on the surface on the back side on the side with which the distal end surface of the duct contacts.

(12) The connector according to the above-described item (7) or (8), in which the pressed section has a flat surface on the side with which the distal end surface of the duct contacts.

(13) The connector according to any one of the above-described items (1) to (6), in which the valve disc has a pressed section provided with a slit section opened upon the natural state and the shape of the valve disc is regulated by the connecting member upon the non-connection between the duct and the connector main body so that the slit section is closed.

(14) The connector according to the above-described item (13), in which a contour in plan view of the pressed section has a non-circular shape upon the natural state, and the shape of the valve disc is regulated by means of the connecting member to become substantially circular.

(15) The connector according to the above-described item (7), in which the pressed section has a first convex section on the side with which the distal end surface contacts.

(16) The connector according to the above-described item (15), in which the first convex section is formed into a substantially dome shape.

(17) The connector according to the above-described item (15) or (16), in which the pressed section has a second convex section projecting opposite the first convex section on the back side of the first convex section.

(18) The connector according to the above-described item (17), in which the second convex section is formed into a substantially hemispherical shape.

(19) The connector according to any one of the above-described items (1) to (18), in which the fluid passage distance of the connector main body defined between the contact surface between the duct and the valve disc disposed at one end of the connector main body and an opening on the other end does not substantially vary with the opening/closing of the valve disc before and after the connection between the duct and the connector main body.

(20) The connector according to any one of the above-described items (1) to (19), in which the volume of the fluid passage of the connector main body does not substantially vary before and after the connection between the duct and the connector main body.

BRIEF DESCRIPTION OF THE DRAWINGS

FIG. 19 is a side sectional view in accordance with a sixth embodiment of a connector of the present invention, which shows a state that a duct is not connected.

FIG. 20 is a side sectional view in accordance with the sixth embodiment of the connector of the present invention, which shows a state that the duct is connected.

FIG. 21 is a side sectional view showing another example in which a plurality of connectors according to the present invention are provided.

BEST MODE FOR EMBODYING THE INVENTION

A connector according to the present invention will now be described in detail on the basis of preferred embodiments with reference to the accompanying drawings. The modes of the present invention are not limited to the embodiments shown.

Figure 1:
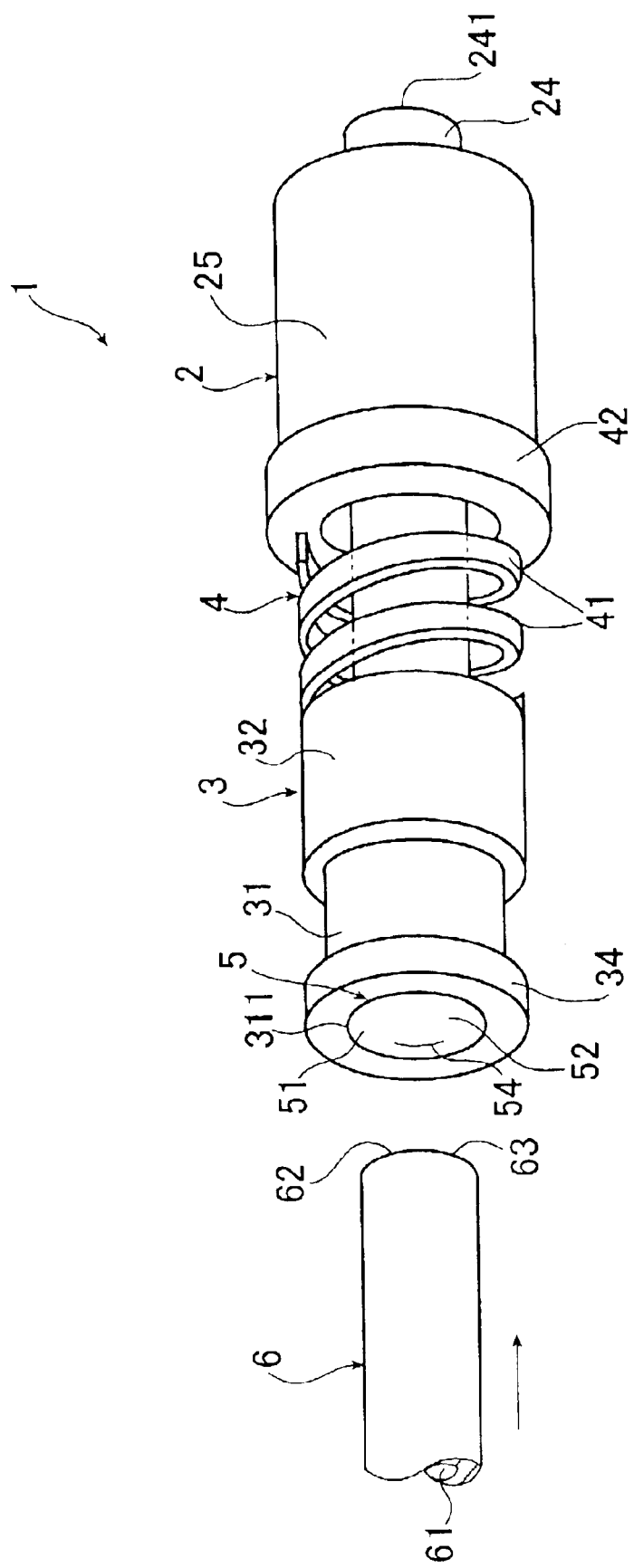
FIG. 1 is a perspective view in accordance with a first embodiment of a connector of the present invention, which shows a state that a duct is not connected.
Figure 2:
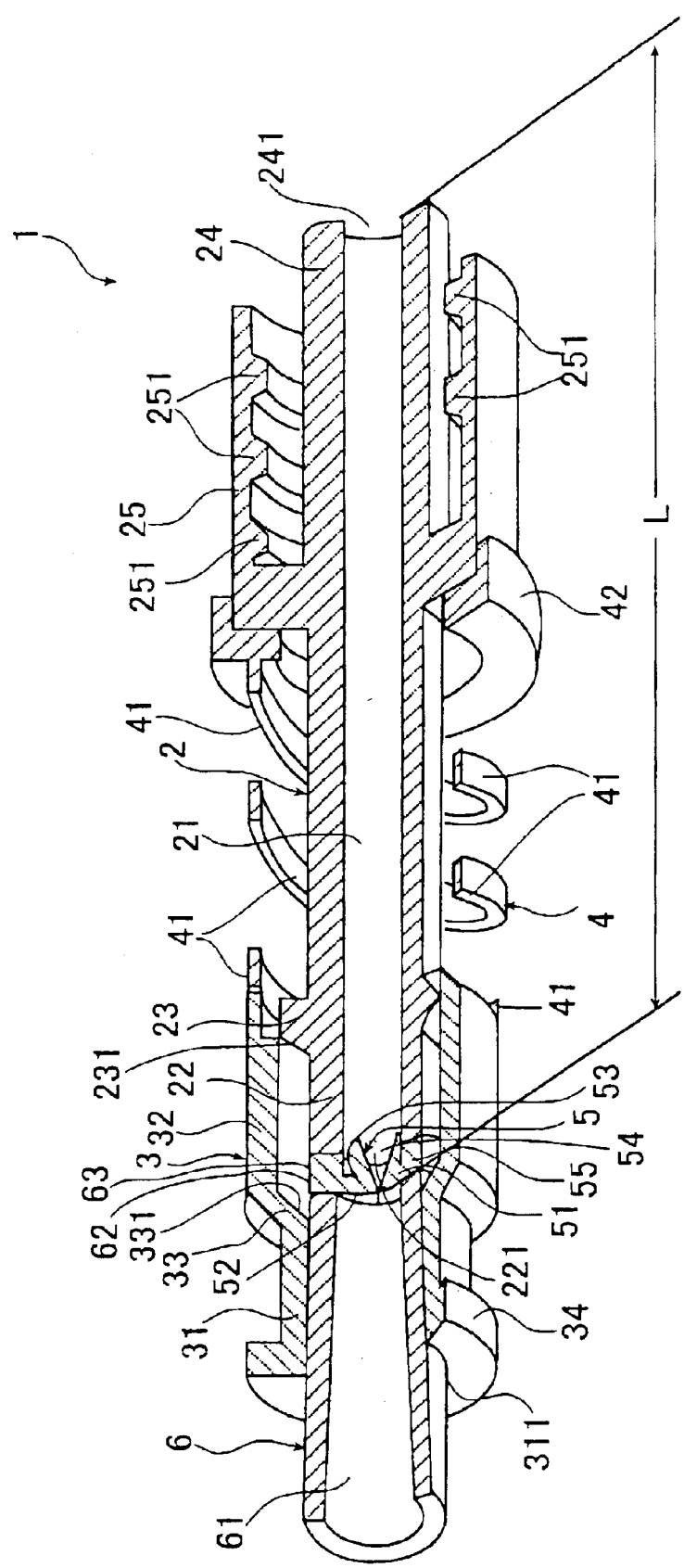
FIG. 2 is a perspective view in accordance with the first embodiment of the connector of the present invention, which shows a state that the duct is connected.
Figure 3:
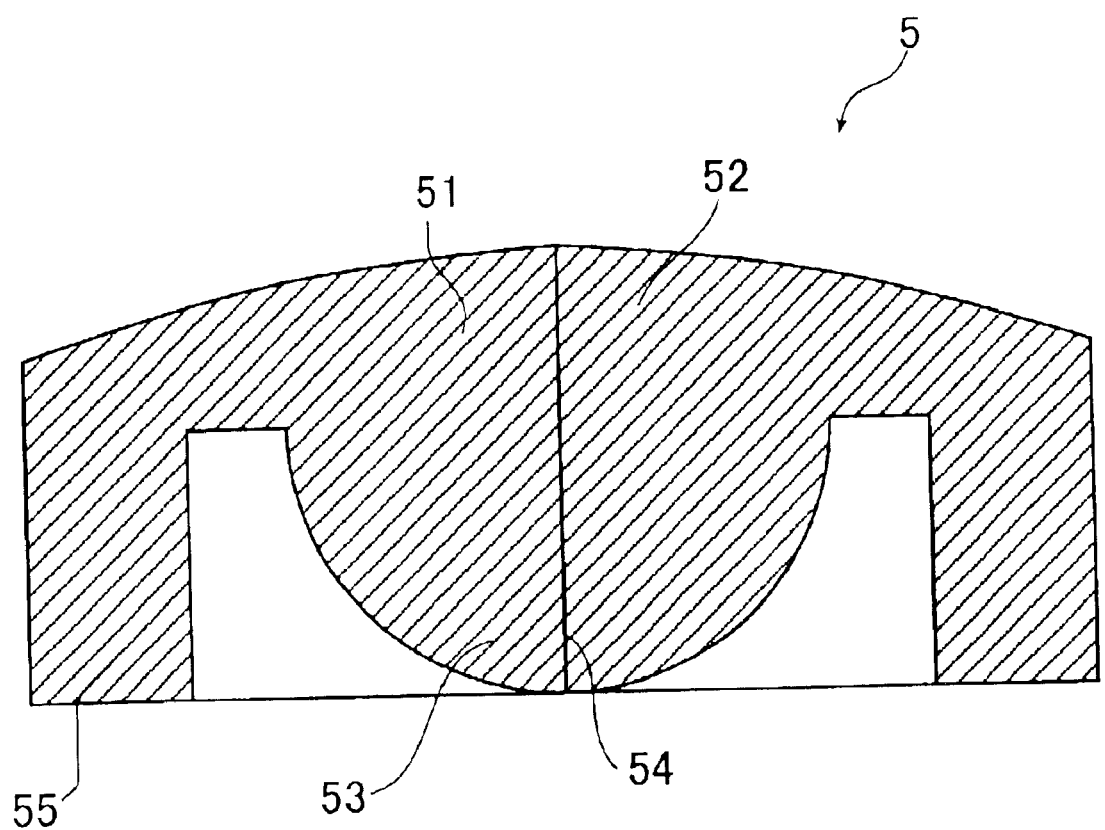
FIG. 3 is a sectional view showing a structural example of a valve disc according to the present invention.

A first mode of the connector according to the present invention is shown in FIGS. 1 to 3. The connector 1 according to the present invention is provided with: a substantially cylindrical connector main body 1 having a fluid passage (hereinafter referred to as a flow path) 21 in its interior and opened at both ends (241 and 221); a valve disc 5 disposed at the opening end 221 that is one of the openings of the connector main body 2 and made of elastic material for opening the flow path 21 within the connector main body 2 upon the connection with a duct 6 to be connected to the connector main body 2 and closing upon the non-connection; and a substantially cylindrical duct connecting member 3 disposed on the outer periphery of the connector main body 2 on the side of the valve disc 5 and coaxially with the connector main body 2 to be movable in an axial direction of the connector main body 2.

An inner diameter (diameter of the flow path 21) of the connector main body 2 according to the present invention is usually substantially equal to an outer diameter of a tip end section of the duct 6 to be connected and never greater than the outer diameter. Accordingly, the duct 6 to be connected is no longer substantially inserted into the flow path 21 through the valve disc 5.

Incidentally, for the sake of the explanation, the explanation will be given by regarding the side of the valve disc 5 (for example, the left side on the paper surface of FIGS. 1 and 2 and FIGS. 4 to 9) as a "proximal end" and the opening side (right side on the paper surface) as a "distal end" with respect to a longitudinal direction (horizontal direction on the paper surface) of the cylindrical connector main body 1. The other drawings are based on this rule.

The connector according to the first mode will now be described in more detail.

FIG. 1 is a perspective view showing a state that the duct 6 is not connected to the connector 1. FIG. 2 is a sectional perspective view showing a state that the duct 6 is connected thereto.

The connector 1 connects the duct 6 and has the substantially cylindrical connector main body 2, the substantially cylindrical connecting member 3, a connecting section 4 whereby the connector main body 2 and the connecting member 3 are connected with each other and the valve disc 5 formed of elastic material (flexible material).

As shown in FIGS. 1 and 2, the connector main body 2 has the flow path 21 in its interior, and the valve disc 5 is disposed at the end of the opening 221 on the side of a proximal end section 22 of the flow path 21.

A ring-shape retainer section 23 that may be brought into contact with a stepped section 33 of the connecting member 3 to be described later is provided on an outer peripheral surface of the proximal end section 22 of the connector main body 2, and a taper surface 231 that has an outer diameter decreasing gradually from the distal end to the proximal end is formed on the proximal end side of the retainer section 23. Upon the non-connection of the duct 6, the taper surface 231 and a taper surface 331 of the stepped section 33 are engaged with each other so that the connecting member 3 is regulated in position and retained at a predetermined position relative to the connector main body 2.

A taper surface that has an outer diameter decreasing gradually from the proximal end to the distal end is formed on an outer peripheral surface of the distal end section 24 of the connector main body 2; that is, the outer peripheral side of the distal end section 24 is formed into a lure taper-shape.

The side of the distal end section 24 of the connector main body 2 is formed into a double sleeve shape and has a substantially cylindrical (outer sleeve) lure lock section 25 having a greater diameter than that of the distal end section 24. A spiral rib (lure lock screw) 251 is formed in an inner peripheral surface of the lure lock section 25.

A tube (not shown) having, for example, flexibility and the like are connected liquid-tightly through a predetermined jig or directly on the distal end side of this connector main body 2 whereby the flow path 21 of the connector main body 2 and the inner hole (not shown) of the tube are in communication with each other. A tube of an infusion set, for example, is given as this tube. The distal end section 24 of the connector main body 2 may be inserted into and connected to the tube. Also, the distal end section 24 of the connector main body 2 may be fit to the tube and at the same time, a flange or a lure lock screw (neither shown) on the tube side may be threadedly engaged and locked by the rib 251 of the lure lock section 25.

Incidentally, according to the present invention, the lure lock section 25 may be dispensed with. Also, the outer diameter of the distal end section 24 of the connector main body 2 may be kept constant in the axial direction (longitudinal direction).

The connector 1 has the connecting member 3 disposed on the outer side of the connector main body 2 and movable in the axial direction of the connector main body 2.

The connecting member 3 is composed of a proximal end section 31 that is a connecting port section (connecting section) for the duct 6 and a distal end section 32 having a greater diameter than that of the proximal end section 31. Normally, the duct 6 to be inserted into the connecting member has an outer diameter decreasing gradually toward the distal end. The proximal end section 31 has an inner diameter that may allow the insertion length of the duct 6 in which the distal end of the duct 6 pushes and opens the valve disc 5 of the connector main body 2 and maintain the duct 6 stably. Also, the inner diameter of this proximal end section 31 is smaller than the inner diameter of the distal end section 32, somewhat greater than the outer diameter of the distal end section 24 of the connector main body 2 and smaller than the outer diameter of the retainer section 23 of the connector main body 2. The inner diameter of the distal end section 32 is somewhat greater than the outer diameter of the retainer section 23 of the connector main body 2.

The stepped section 33 is formed at a boundary (boundary section) of the proximal end section 31 and the distal end section 32. The taper surface 331 that has an inner diameter decreasing from the distal end to the proximal end is formed on the inner peripheral side of this stepped section 33.

A position regulating means for regulating the position of the connecting member 3 is defined by this stepped section 33 and the retainer section 23 of the above-described connector main body 2.

Also, a ring-shape flange 34 is formed on the proximal end of the connecting member 3. This flange 34 is threadedly engaged with the lure lock screw (not shown) on the duct 6 side so that the duct 6 is locked relative to the connecting member 3. Alternatively, instead of the flange 34 shown, it is possible to form a spiral rib (lure lock screw) to threadedly engage with the lure lock screw (not shown) on the duct 6 side on the outer peripheral surface of the proximal end section 31 of the connecting member 3.

Also, according to the present invention, the flange 34 of the connecting member 3 or the rib may be dispensed with.

The connecting member 3 is connected with the connector main body 2 by a connecting section 4.

The connecting section 4 is constituted of a spiral spring (biasing means) 41 and a ring-shape attaching section 42 formed at a tip end of this spring 41.

The proximal end of the spring 41 is bonded to a tip end of the above-described connecting member 3, and the attaching section 42 is bounded to a proximal end of the lure lock section 25 of the connector main body 2.

As a joint method, fitting (particularly fitting or threadedly engagement with caulking), adhesion with adhesives and so on are exemplified. Also, in the case where the members connected with each other are made of resin, it is possible to adopt melt-bonding such as melt-bonding by heat or melt-bonding by ultrasonic wave.

Here, it is preferable to integrally form the connector main body 2 and/or connecting member 3 with the connecting section 4. In particular, it is preferable to integrally form the connecting member 3 with the connecting section 4. Thus, it is possible to decrease the number of parts and also to reduce labor upon the assembling work and time required for assembly.

The spring 41 is set up so as to be extended to some extent from the non-loaded state (natural length) upon the connection between the duct 6 and the connector 1 and biases the connecting member 3 toward the tip end side (in a direction close to the connector main body 2) relative to the connector main body 2, i.e., toward the side of the connector main body 2 by its restoring force (elastic force).

The valve disc 5 is fixed liquid-tightly (airtightly) to the proximal end opening 221 of the connector main body 2 so as to close the flow path 21.

In FIG. 2, the distal end of a base body section 55 of the valve disc 5 is bonded to the opening 221 end section of the connector main body 2. As a joint method for connecting the valve disc 5 and the connector main body 2, the fitting (particularly fitting or threadedly engagement with caulking), adhesion with adhesives and so on are exemplified. Also, in the case where the connector main body 2 is made of resin, it is possible to adopt the melt-bonding such as melt-bonding by heat or melt-bonding by ultrasonic wave.

A structural example of the valve disc is shown in section in FIG. 3. The valve disc 5 is composed of the substantially cylindrical base body section 55 and a pressed section 51 provided to shield the inner hole of the base body section 55 on one end side (proximal end side) in the axial direction of the base body section 55. It is preferable to integrally form the base body section 55 and the pressed section 51.

The pressed section 51 is a section that receives the pressure from the distal end surface 62 of the duct 6 and its central section is formed into a thick section thicker than the outer periphery.

This pressed section 51 has a first convex section 52 with which a distal end surface 62 of the duct 6 is brought into contact. This first convex section 52 is formed into a substantially dome-shape (conical, bevel, plate-like or the like) and projects by a predetermined amount (is exposed to the connecting port) from the proximal end opening 311 of the connecting member 3 to the outside when the duct 6 is not connected to the connector 1 (joint port).

Also, the pressed section 51 has a second convex section 53 on the back side of the first convex section 52. This second convex section 53 is formed into a substantially hemispherical shape and projects opposite the first convex section 52.

Thus, the pressed section 51 preferably has a curved convex surface on at least one of the surface (surface on the proximal end side) on the side with which the distal end surface 62 of the duct 6 is brought into contact and the surface (surface on the distal end side) on its back side, and more preferably has curved convex surfaces on the surface on the side with which the distal end surface 62 of the duct 6 is brought into contact and the surface on the back side, respectively. Thus, the liquid-tightness (airtightness) may be further enhanced.

A slit section 54 passing through the pressed section 51 is formed in the central section (thick section) of such a pressed section 51. In this embodiment, the slit section 54 is comprised of a straight-line cut (slit) formed to pass through the apexes of the first convex section 52 and the second convex section 53.

This slit section 54 is closed by the elasticity of the pressed section 51 to hold the liquid-tight state (airtight state) in the non-loaded state (the state that the external force is not applied).

Incidentally, according to the present invention, the shape of the slit of the slit section 54 is not limited to that shown in the drawings but may be a cross shape, for example.

Figure 13A:
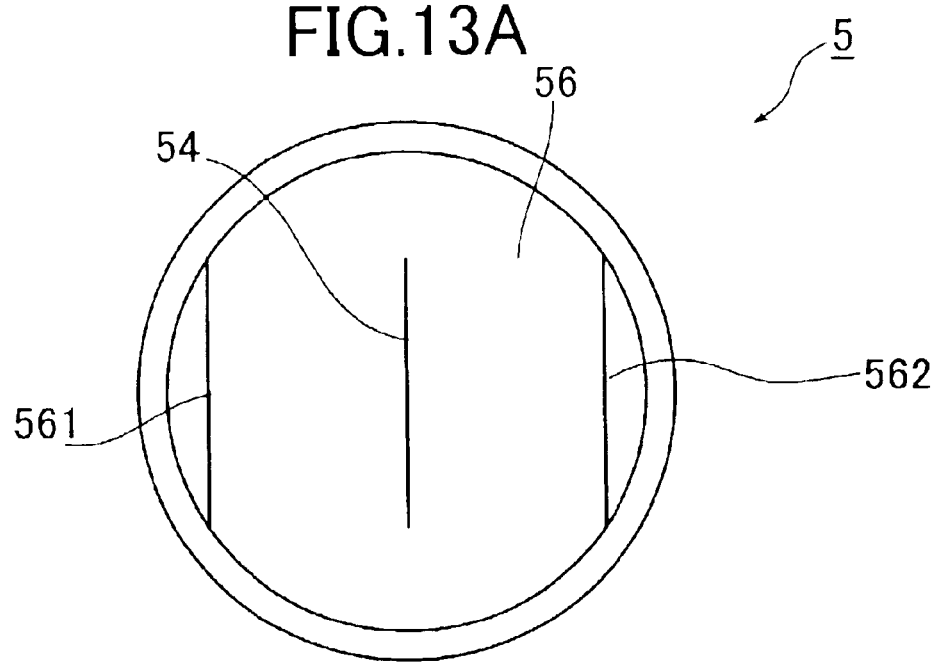
FIGS. 13A and 13B are a plan view and a local sectional view of a side surface showing an structural example of a valve disc according to the present invention.
Figure 13B:
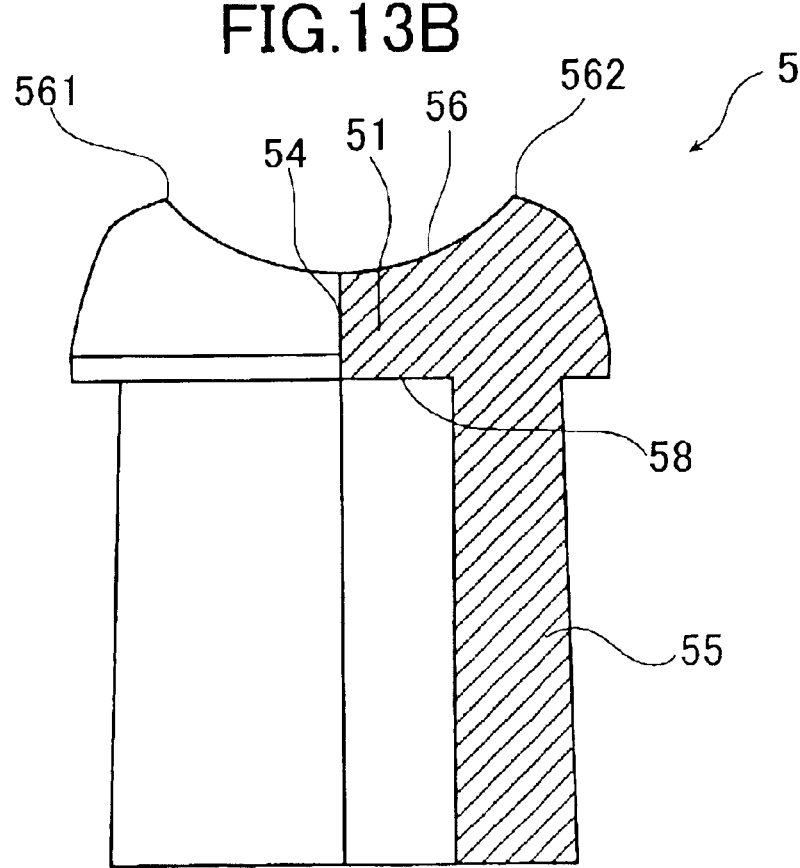

Also, according to the present invention, the surface (surface on the distal end side) on the back side to the side, with which the distal end surface 62 of the duct 6 is brought into contact, of the pressed section 51 may be flat (see FIG. 13B).

Also, according to the present invention, the shape of the pressed section 51 is not limited to that shown or described above. For example, it is possible to obtain the sufficiently high liquid-tightness (airtightness) even without using the shape of the pressed section 51 shown according to a kind of fluid flowing through the flow path 21 of the connector 1, a magnitude of the pressure (inner pressure of the flow path 21) from the flow path 21 side of the connector main body 2, and the like. In this case, for example, a relatively small rib is provided to the pressed section 51 or a thickness of the pressed section 51 (section where the slit section 54 is formed) is set up (adjusted) to a suitable value.

Also, according to the present invention, for example, in the case where the duct 6 is not connected to the connector 1 (connecting port), it is possible to take a structure in which a position in the axial direction of the apex section of the first convex section 52 and a position in the axial direction of the proximal end of the connecting member 3 are substantially identified with each other.

Examples of the structural materials of the connector main body 2, the connecting member 3, and the connecting section 4 include: polyolefines such as a polyethylene, a polypropylene, an ethylene-propylene copolymer, and an ethylene-vinyl acetate copolymer (EVA); a polyvinyl chloride, a polyvinylidene chloride, a polystyrene, a polyamide, a polyimide, a polyamide imide, a polycarbonate, a poly(4-methylpentene-1), an ionomer, an acrylic resin, a polymethyl methacrylate, an acrylonitrile-butadiene-styrene copolymer (ABS resin), an acrylonitrile-styrene copolymer (AS resin), a butadiene-styrene copolymer; polyesters such as a polyethylene terephthalate (PET), a polybuthylene terephthalate (PBT), and polycyclohexane terephthalate (PCT); a polyether, a polyetherketone (PEK), a polyetheretherketone (PEEK), a polyetherimide, a poly-acetal (POM), a polyphenylene oxide, a modified polyphenylene oxide, a polysulfone, a polyethersulfone, a polyphenylene sulfide, a polyarylate, an aromatic polyester (liquid crystal polymer), polytetrafluoroethylene, polyvinylidene fluoride; various resin materials such as other fluorine resins; and a blend product and a polymer alloy containing at least one of the above-mentioned materials. Further, various glass materials, ceramic materials, and metal materials may also be used.

In the case where the connector main body 2, the connecting member 3 and the connecting section 4 are made of resin, respectively, it is possible to form them into a desired shape with ease by means of, for example, injection molding.

Moreover, the valve disc 5 consists of an elastic material (flexible material) which is elastic deformable. Examples of the material include: various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluorine rubber; various thermoplastic elastomers such as styrene-based, polyolefin-based, polyvinyl chloride-based, polyurethane-based, polyester-based, polyamide-based, polybutadiene-based, trans-polyisoprene-based, fluorine rubber-based, and chlorinated polyethylene-based thermoplastic elastomers. Those materials may be used alone or in combination of at least two of the above-mentioned materials.

The duct 6 is a section or an equipment to be connected to the connecting port (proximal end section 31 of the connecting member 3) of the connector 1. As the duct 6, there is exemplified a tubular equipment such as a tip end projecting section (section to which a needle tube is connected) of a syringe (injection syringe) or a hub or sheath that is independent by itself.

The duct 6 has a flow path 61 in its interior. Then, a taper surface that has an outer diameter decreasing from the proximal end to the distal end is formed on the outer peripheral side of the duct 6. That is, the outer peripheral side of the duct 6 is formed into a lure taper shape.

The outer diameter of a tip end 63 of the duct 6 is somewhat smaller than the inner diameter (connecting diameter) of the proximal end section 31 of the connecting member 3, and the outer diameter of the proximal end of the duct 6 is greater than the inner diameter of the proximal end section 31. Thus, it is possible to insert the tip end section of the duct 6 into the connecting member 3 from the opening 311 and to insert (fit) it into the proximal end section 31 at a desired depth.

As the structural material for the duct 6, there can be used the same material as that for the structural material of the connector main body 2, the connecting member 3 and the connecting section 4.

The operation of the connector 1 will now be described.

As shown in FIG. 1, when the duct 6 is not connected to the connector 1 (connecting port) (upon non-connected state), the connecting member 3 is biased toward the tip end side relative to the connector main body 2, i.e., toward the connector main body 2 by the restoring force (elastic force) of the spring 41, and the stepped section 33 of the connecting member 3 is retained by the retainer section 23 of the connector main body 2 whereby the position of the valve disc 5 is regulated (retained) such that the first convex section 52 project to the outside from the proximal end of the connecting member 3 by a predetermined amount.

Thus, since the first convex section 52 of the valve disc 5 projects to the connecting port upon the non-connected state, it is possible to, for example, clean or wipe the surface of the first convex section 52 of the valve disc 5 to thereby make it possible to keep clean the surface of the first convex section 52.

Also, the slit section 54 of the valve disc 5 is biased such that the slit section 54 is closed by the elastic force of the pressed section 51 upon the non-connected state, i.e., the non-loaded state (state that the external force is not applied) to thereby keep the closed state and to keep the liquid-tightness (airtightness).

In this case, since the pressure (inner pressure of the flow path 21) from the flow path 21 side of the connector main body 2 is applied so as to close the slit section 54 in the same manner as the elastic force of the pressed section 51, it is possible to positively prevent the leakage of the fluid (liquid, gas or the like) from the slit section 54.

As shown in FIG. 1, when the duct 6 is connected to the connector 1 (connecting port), the positioning is carried out such that the axis of the duct 6 and the axis of the connector 1 (opening 311) coincide with each other.

Then, the duct 6 in this state is moved to the distal end side (in a direction indicated by the arrow in FIG. 1), and is inserted into the connector 1 (connecting member 3) from the opening 311 of the connecting member 3. At this time, the connecting member 3 is moved in a direction away from the connector main body 2 (proximal end side) against the elastic force of the spring 41.

Thus, as shown in FIG. 2, the spring 41 is elongated, and the pressed section 51 (first convex section 52) of the valve body 5 is pressed by the distal end surface 62 of the duct 6. The first convex section 52 undergoes elastic deformation, a dome shape thereof is gradually changed to a flat shape, and the first convex section 52 is warped (the surface of the pressed section 51 becomes a concave shape).

Along with the change in the shape of the pressed section 51, the slit section 54 that has been closed gradually opens from the second convex section 53 side, and finally opens at a predetermined opening. Thus, the flow path 61 of the duct 6 is made to communicate with the flow path 21 of the connector main body 2 (flow path of the connector).

As described above, the duct 6 is connected to the connector 1.

As shown in FIG. 2, when the duct 6 is connected to the connector 1 (connected state), the distal end surface 62 of the duct 6 is brought into airtight (liquid-tight) contact with the valve disc 5. In this case, the spring 41 is elongated more than that in the case of the non-connected state, the valve disc 5 is pressed against the duct 6 by its restoring force whereby the sealability (liquid-tightness, airtightness) between the duct 6 and the valve disc 5 is considerably enhanced to thereby make it possible to positively prevent the liquid leakage or the like.

Also, under the connected state, the duct 6 is fit to the proximal end section 31 at a position where its outer diameter coincides with the inner diameter (diameter of the opening 311) of the proximal end section 31 of the connecting member 3 that is the connecting port. Thus, it is possible to prevent the duct 6 from being easily removed away from the connector 1.

Also, in the connector 1, when the duct 6 is connected to the connector 1, the connecting member 3 moves in a direction away from the connector main body 2. Thus, since it is possible to open the valve disc 5 and make the flow path 61 of the duct 6 communicate with the flow path 21 of the connector main body 2 without invasion of the distal end surface 62 of the duct 6 or the outer peripheral surface of the tip end section into the flow path 21 of the connector main body 2 exceeding the valve disc 5 (without insertion of the duct 6 into the valve disc 5), the volume (flow path volume) of the flow path 21 of the connector main body 2 does not substantially vary before and after the connection of the duct 6 (upon the non-connected state and the connected state). Namely, the volume of the flow path 21 does not substantially vary in accordance with the opening/closing of the valve disc 5. Also, the distance L from a tip end 63 of the duct 6 to the fluid passage opening 241 (tip end of the flow path 21) does not substantially vary before and after the connection (non-connected state and connected state) of the duct 6 under the state of contact between the tip end 63 of the duct 6 and the valve disc 5.

For this reason, in the case where the connector 1 is used to be connected to the catheter disposed in the blood vessel, for example, since the volume of the flow path 21 of the connector main body 2 does not substantially vary even if the duct 6 is removed from the connector 1, the blood is no longer sucked into the catheter. Thus, it is possible to prevent (or suppress) the generation of thrombi within the catheter.

Also, when the duct 6 is connected to the connector 1, since this connector 1 does not have the mode in which the distal end surface 62 of the duct 6 or the outer peripheral surface of the distal end section invades the flow path 21 of the connector main body 2 exceeding the valve disc 5 (the duct 6 penetrates through the slit section 54 of the valve disc 5), the disadvantage that the slit section 54 is excessively expanded to degrade the airtightness (liquid-tightness) is not caused. Also, even if foreign matters (refuse, dust or the like), bacilli or the like are adhered to the distal end surface 62 of the duct 6 or the outer peripheral surface of the distal end section, it is possible to prevent the foreign matters or the like from entering the flow path 21 of the connector 2 and contaminating the interior of the flow path 21.

When the duct 6 is removed from the connector 1, the duct 6 in the state shown in FIG. 2 is moved to the proximal end side and pulled apart from the connecting member 3.

Thus, since the pressure applied to the valve disc 5 by the duct 6 is released, the valve disc 5 is restored back to the original shape immediately by the self-restoring force due to its elasticity and brought into the above-described state shown in FIG. 1.

As shown in FIG. 1, when the valve disc 5 is returned back to the original shape, the slit section 54 is again closed and restores its airtightness (liquid-tightness) as mentioned above. Thus, after the duct 6 is removed away from the connector 1, even if, for example, the fluid flows in the reverse direction toward the proximal end, it is possible to prevent the fluid from flowing out (leaking) from the proximal end side of the connector 1.

In particular, in this embodiment, since the slit section 54 is formed in the first convex section 52 and the second convex section 53 that are the thick sections, it is possible to further enhance the sealability upon the closing of the slit section 54 compared with the case where the slit section 54 is formed in the flat section. It is therefore possible to more positively prevent the liquid leakage against the elevation of the inner pressure of the flow path 21 of the connector main body 2, or the like.

Also, since the connecting member 3 is biased toward the connector main body 2 by the restoring force of the spring 41, when the duct 6 is removed away from the connecting member 3, the connecting member 3 is moved to the distal end relative to the connector main body 2. In this case, since the taper surface 331 is formed on the inner peripheral side of the stepped section 33 of the connecting member 3, the connecting member 3 may smoothly move along the taper surface 331.

Then, the stepped section 33 of the connecting member 3 is brought into abutment with the retainer section 23 of the connector main body 2. Thus, the connecting member 3 is stopped (the connecting member 3 is returned immediately back to the original position). That is, as described above, the stepped section 33 of the connecting member 3 is retained by means of the retainer section 23 of the connector main body 2. Thus, the connecting member 3 is positioned to the connector main body 2 (valve disc 5) such that the first convex section 52 of the valve disc 5 projects from the proximal end of the connecting member 3 to the outside by a predetermined amount and brought into the above-described state shown in FIG. 1.

The above-described effect can be obtained by the connector 1.

Also, the connector does not have a mode in which the duct 6 is connected so as to pass through the slit section 54 of the valve disc 5 as described above. Accordingly, the slit section 54 is not excessively expanded. As a result, even if the removal of the duct 6 to the connector 1 is repeatedly performed many times, the sealability of the valve disc 5 in the slit section 54 is hardly degraded.

Also, since the connector 1 does not have a mode in which the valve disc 5 is moved within the flow path 21, it is unnecessary to provide a vent hole (through-hole) for making the flow path 21 communicate with the outside. It is thus possible to prevent the contamination of the interior of the flow path 21 of the connector main body 2.

Also, in the connector 1, since the duct 6 is connected directly and used without using a needle, there arises no problem such as erroneous injection by a medial worker and its safety aspect is high.

Also, in the connector 1, it is possible to perform the attachment/detachment of the duct with a slight force, which is superior in operationability.

Also, in the connector 1, the connecting member 3 is adapted to move in the axial direction to the connector main body 2, so that the number of parts may be reduced relatively to thereby make it possible to simplify the structure. Thus, it is possible to reduce the labor in assembling and to reduce the time required for assembling.

Also, the connector 1 is advantageous of miniaturization. For example, it is possible to apply the connector with ease to the tube in an infusion set, a chemicals feed inlet or the like.

Other modes of a connector according to the present invention will now be described. In the following modes, the same reference numerals are used to indicate the parts that are same as or corresponding to those in FIGS. 1 to 3. The explanation will be omitted for the common points indicated by the same reference numerals and only the main difference will be explained.

A second embodiment of a connector according to the present invention will now be described with reference to FIGS. 4 and 5.

Figure 4:
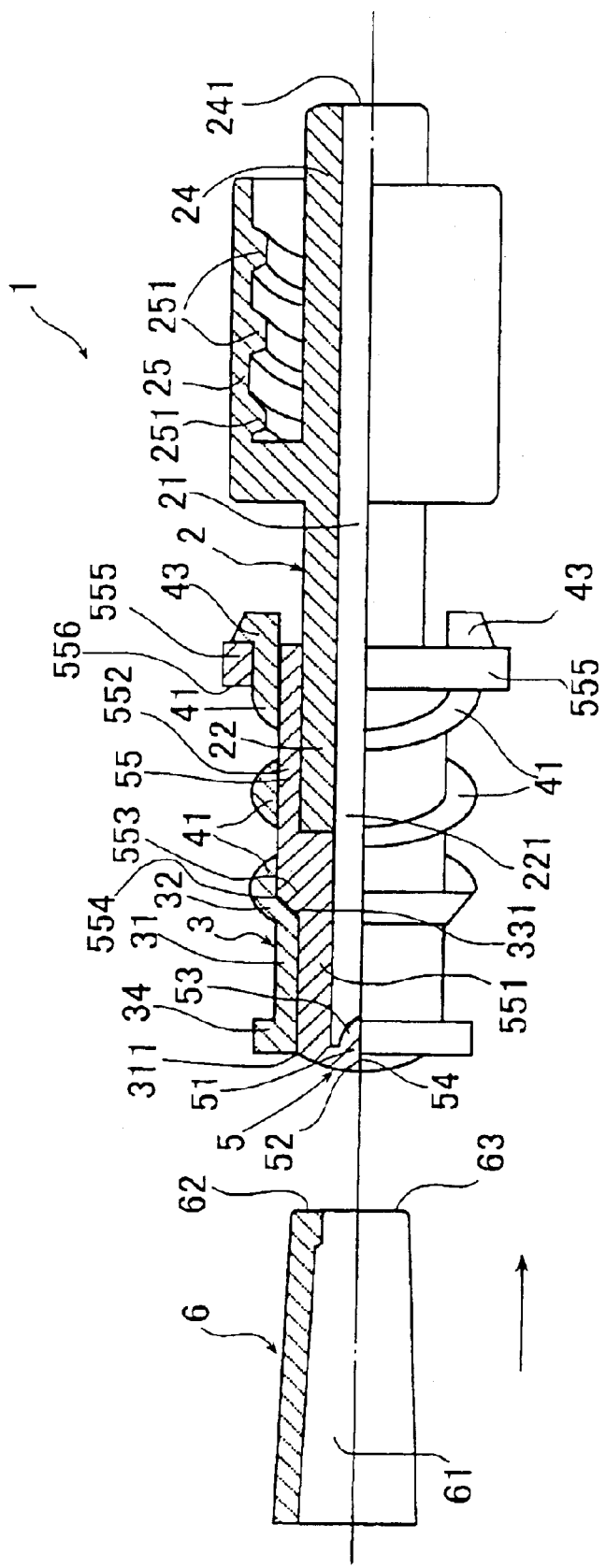
FIG. 4 is a local sectional view of a side surface in accordance with a second embodiment of a connector of the present invention, which shows a state that a duct is not connected.
Figure 5:
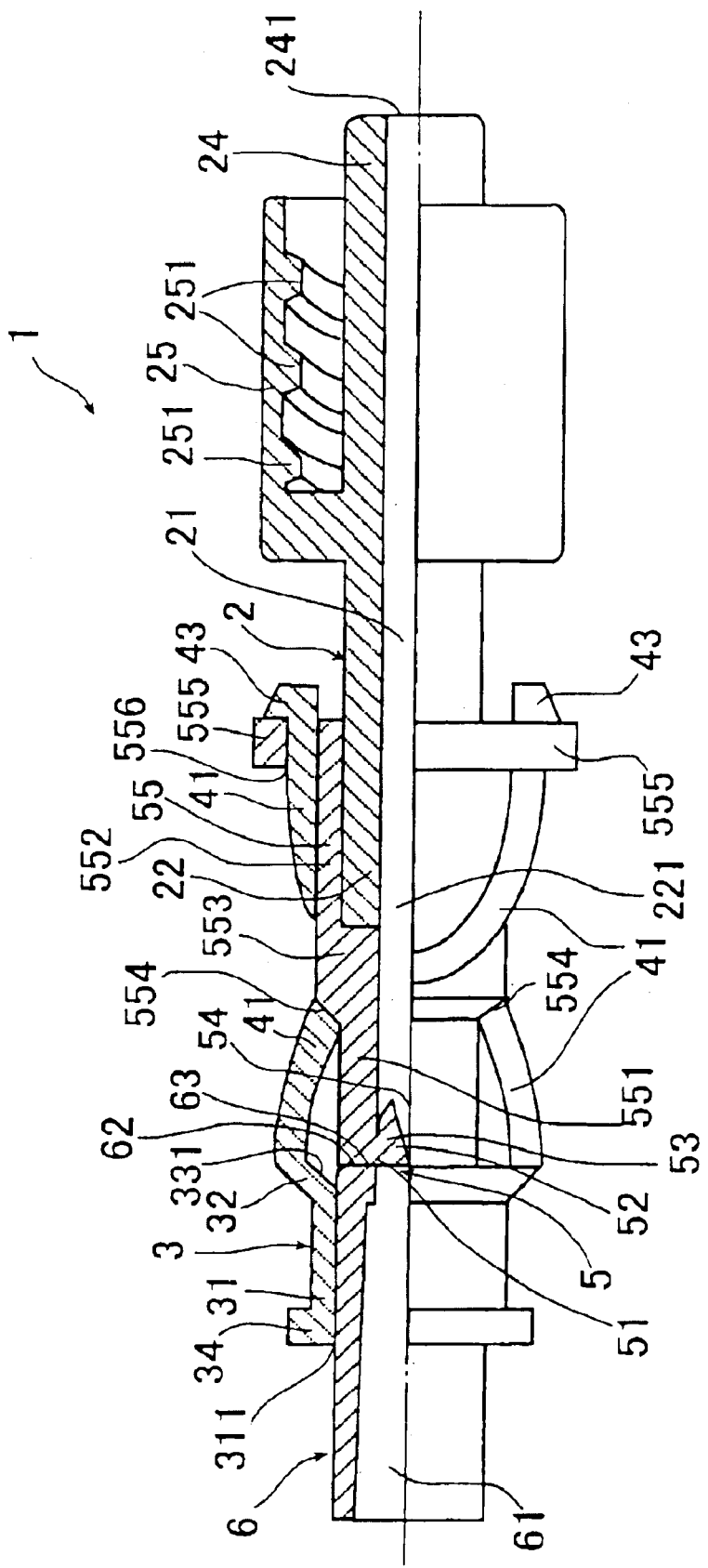
FIG. 5 is a local sectional view of a side surface in accordance with the second embodiment of the connector of the present invention, which shows a state that the duct is connected.

FIG. 4 is a local sectional view of a side surface of the connector according to the present invention, which shows the state that the duct 6 is not connected to the connector 1 of the second embodiment. FIG. 5 is a local sectional view of a side surface, which shows the state that the duct 6 is connected to the connector 1.

In the connector 1 shown in these drawings, the outer diameter of a proximal end section 551 of the base body section 55 of the valve disc 5 is smaller than the outer diameter of a distal end section 552.

A stepped section 553 that may retain the distal end section 32 of the connecting member 3 to be described later (that may come into contact with the distal end section 32) is formed at a boundary (boundary section) of the proximal end section 551 and the distal end section 552. A taper surface 554 that has an outer diameter decreasing from the distal end to the proximal end is formed on the outer peripheral side of the stepped section 553.

A ring-shape rib 555 is formed at a tip end of the base body section 55. A hole section 556 passing in the axial direction is formed in this rib 555.

A stepped section is formed in the distal end section 32 of the connecting member 3. The taper surface 331 having an inner diameter decreasing from the distal end to the proximal end is formed on the inner peripheral side of this distal end section 32.

A position regulating means for regulating the position of the connecting member 3 is defined by this distal end section 32 and the stepped section 553 of the valve disc 5.

The connecting section 4 is constituted of the spiral spring (biasing means) 41 and an engagement claw 43 formed at the tip end of this spring 41.

The proximal end of the spring 41 is bonded to the tip end of the connecting member 3.

On the other hand, the tip end section of the spring 41 is inserted into the hole section 556 of the rib 555 of the valve disc 5, and the engagement claw 43 is engaged with the rib 555 under this state to thereby connect the distal end section of the spring 41 to the rib 555 of the valve disc 5.

Namely, the valve disc 5 and the connecting member 3 are connected with each other by means of this connecting section 4.

Incidentally, as described in conjunction with the connector 1 according to the above-described first embodiment, it is preferable to integrally form the connecting member 3 and the connecting section 4 also in this connector 1.

As described above, according to this connector 1, it is possible to obtain the same effect as that of the connector 1 in the above-described first embodiment.

Also, it is possible to easily connect the valve disc 5 and the connecting member 3 by the connecting section 4 even without using adhesive technology or the like. Thus, it is possible to assemble the connector 1 with ease.

Figure 6:
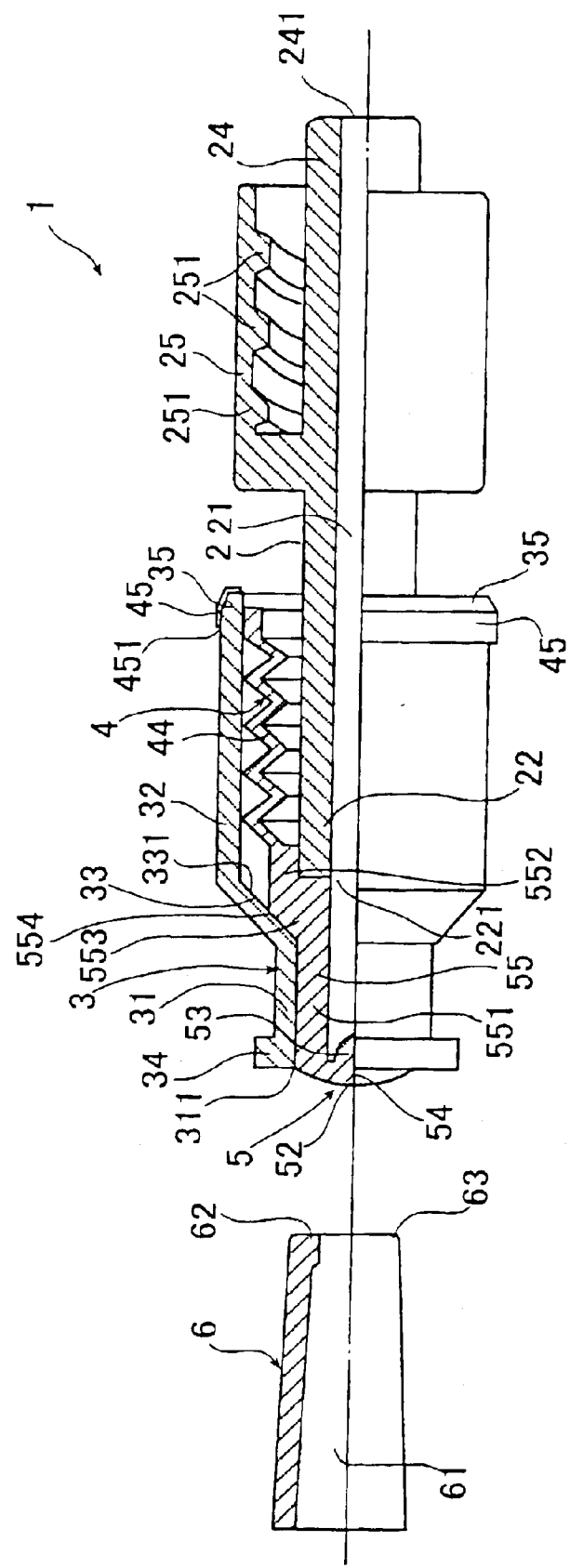
FIG. 6 is a local sectional view of a side surface in accordance with a third embodiment of a connector of the present invention, which shows a state that a duct is not connected.
Figure 7:
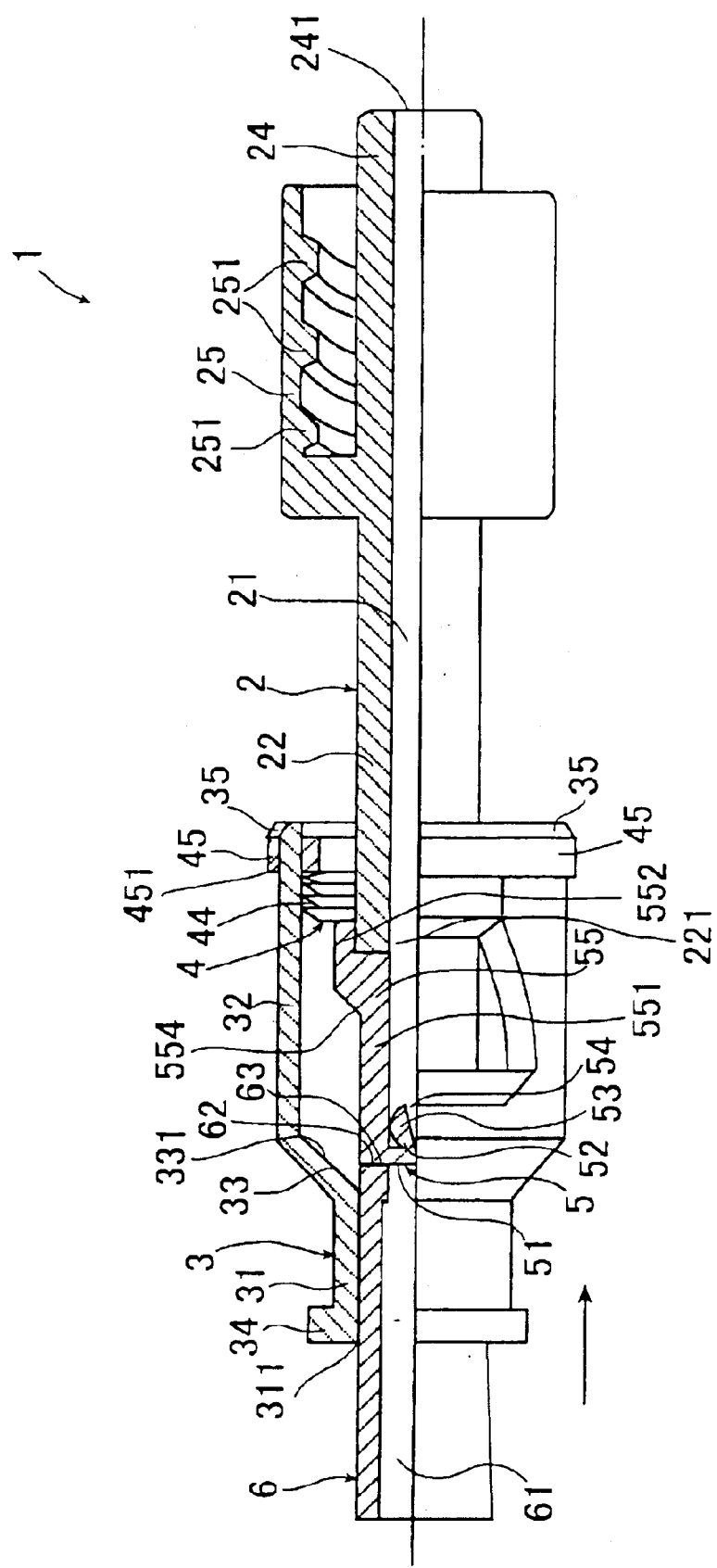
FIG. 7 is a local sectional view of a side surface in accordance with the third embodiment of the connector of the present invention, which shows a state that the duct is connected.

A third embodiment of a connector according to the present invention will now be described with reference to FIGS. 6 and 7. FIG. 6 is a local sectional view of a side surface, which shows the state that the duct 6 is not connected to the connector 1 of the third embodiment. FIG. 7 is a local sectional view of a side surface, which shows the state that the duct 6 is connected to the connector 1.

In the connector 1 shown in these drawings, the outer diameter of the proximal end section 551 of the base body section 55 of the valve disc 5 is smaller than the outer diameter of the distal end section 552.

A stepped section 553 that may engage with the stepped section 33 of the connecting member 3 (that may come into abutment against the stepped section 33) is formed at a boundary (boundary section) of this proximal end section 551 and the distal end section 552. A taper surface 554 that has an outer diameter decreasing from the distal end to the proximal end is formed on the outer peripheral side of this stepped section 553.

A position regulating means for regulating the position of the connecting member 3 is defined by this stepped section 553 and the stepped section 33 of the connecting member 3.

The connecting section 4 is composed of a bellows-like spring (biasing means) 44 and a ring-like attaching section 45 formed at a tip end of this spring 44. A ring-like slit 451 passing in the axial direction is formed in this attaching section 45.

The spring 44 is disposed under the state that it somewhat shrinks from the non-loaded state (natural length) and biases the connecting member 3 toward the tip end side to the connector main body 2 (in a direction closer to the connector main body 2), i.e., toward the connector main body 2 by its restoring force (elastic force).

A ring-like flange 35 is formed at a tip end of the connecting member 3.

The spring 44 is located in the interior (inside) of this connecting member 3, and the proximal end of the spring 44 is bonded to the tip end of the valve disc 5.

On the other hand, the distal end side of the connecting member 3 is inserted into the slit 451 of the attaching section 45 of the connecting section 4 and the rib 35 is engaged with the attaching section 45 under this state whereby the attaching section 45 of the spring 44 and the distal end side of the connecting member 3 are connected with each other. Namely, the valve disc 5 and the connecting member 3 are connected with each other by means of the connecting section 4.

Incidentally, as described in conjunction with the connector 1 according to the above-described first embodiment, also in this connector 1, it is preferable to integrally form the valve disc 5 and the connecting section 4.

When the duct 6 is connected to the connector 1 (connecting port), as shown in FIG. 7, the connecting member 3 is moved in a direction away from the connector main body 2 (toward the proximal end side) so that the spring 44 shrinks.

As described above, according to this connector 1, it is possible to obtain the same effect as that of the connector 1 of the above-described first embodiment.

Also, in this connector 1, since the spring 44 of the connecting section 4 is located in the interior (inside) of the connecting member 3, there is no fear that anything is brought into direct contact with the spring 44.

It is thus possible to perform the connecting work safely even if the duct 6 having no lock mechanism is to be connected to the connector 1.

Also, since the spring 44 of the connecting section 4 is located in the interior of the connecting member 3, it is possible to take any shape for the outer peripheral shape of the connecting member 3. For instance, it is possible to provide a curved surface or a rib (knurl) or the like corresponding to fingers on the outer peripheral side of the connecting member 3 and to perform with ease a device such as facilitating to grip the connector 1. Also, in this connector 1, it is possible to connect the valve disc 5 and the connecting member 3 with each other with ease by means of the connecting section 4 without using adhesive technology or the like, thereby making it possible to assemble the connector 1 with ease.

A fourth embodiment of a connector according to the present invention will now be described with reference to FIGS. 8 and 9.

Figure 8:
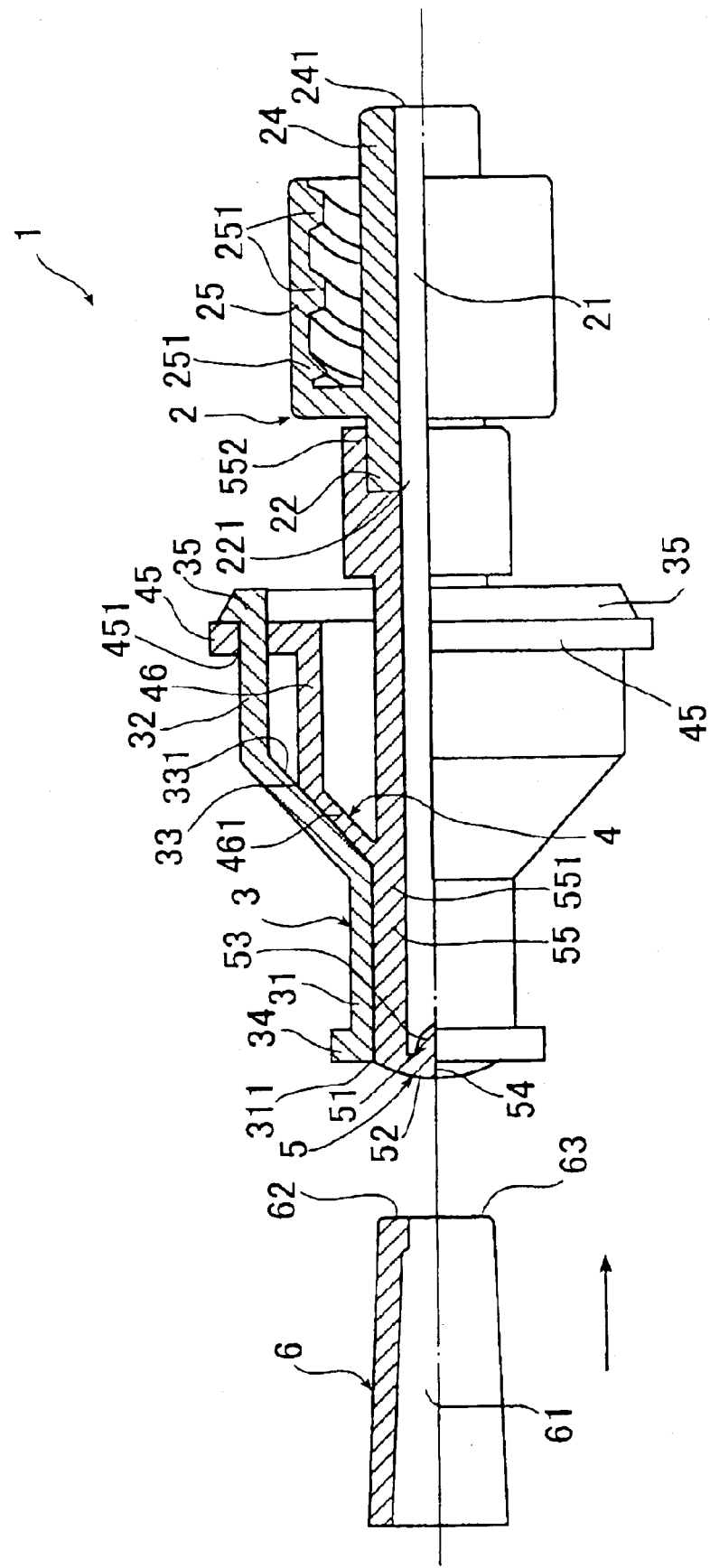
FIG. 8 is a local sectional view of a side surface in accordance with a fourth embodiment of a connector of the present invention, which shows a state that a duct is not connected.

FIG. 8 is a local sectional view of a side surface, which shows the state that the duct 6 is not connected to the connector 1 of the fourth embodiment. FIG. 9 is a local sectional view of a side surface, which shows the state that the duct 6 is connected to the connector 1. Incidentally, the explanation will be omitted for the common points of the connector 1 of the above-described first embodiment and only the main differences will be explained.

In the connector 1 shown in these drawings, the inner diameter of the proximal end section 551 of the base body section 55 of the valve disc 5 is smaller than the inner diameter of the distal end section 552.

The connecting section 4 is composed of a step-like spring (biasing means) 46 and a ring-like attaching section 45 formed at a tip end of this spring 46. A ring-like slit 451 passing in the axial direction is formed in this attaching section 45.

The spring 46 is disposed under the state (shrunk state) that a movable section 461 somewhat bends from the non-loaded state and biases the connecting member 3 toward the tip end side to the connector main body 2 (in a direction close to the connector main body 2), i.e., toward the connector main body 2 by its restoring force (elastic force).

A position regulating means for regulating the position of the connecting member 3 is defined by this movable section 461 of the spring 46 and the stepped section 33 of the connecting member 3.

The ring-like flange 35 is formed at the tip end of the connecting member 3.

The spring 46 is located in the interior (inside) of this connecting member 3, and the proximal end of the spring 46 is bonded to a middle part of the proximal end section 551 of the valve disc 5.

On the other hand, the distal end side of the connecting member 3 is inserted into the slit 451 of the attaching section 45 of the connecting section 4 and the flange 35 is engaged with the attaching section 45 under this state whereby the attaching section 45 of the spring 46 and the distal end side of the connecting member 3 are connected with each other.

Namely, the valve disc 5 and the connecting member 3 are connected with each other by means of the connecting section 4.

Incidentally, as described in conjunction with the connector 1 according to the above-described first embodiment, also in this connector 1, it is preferable to integrally form the valve disc 5 and the connecting section 4.

Figure 9:
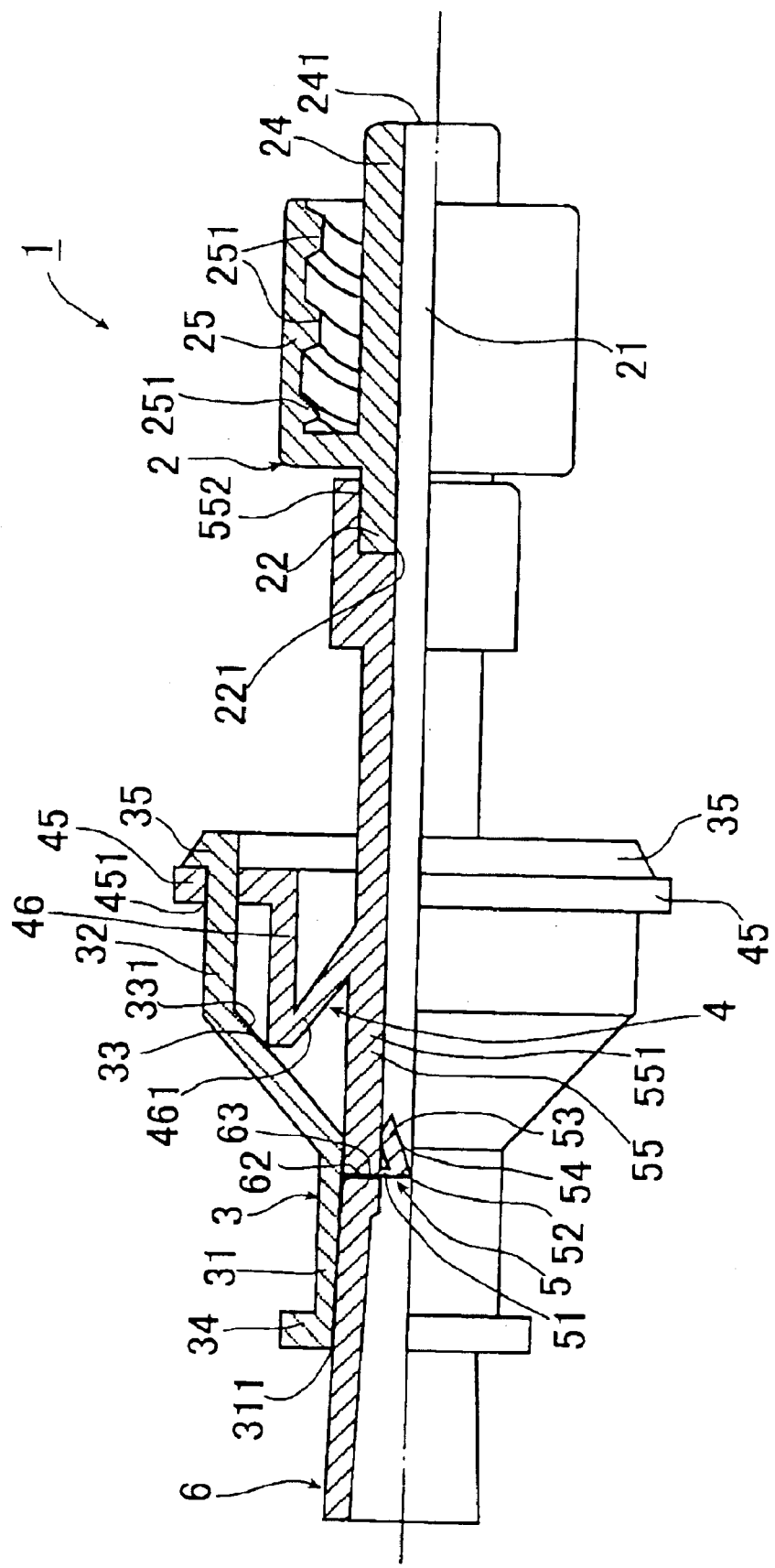
FIG. 9 is a local sectional view of a side surface in accordance with the fourth embodiment of the connector of the present invention, which shows a state that the duct is connected.

When the duct 6 is connected to the connector 1 (connecting port), as shown in FIG. 9, the connecting member 3 is moved in a direction away from the connector main body 2 (toward the proximal end side) so that the movable section 641 of the spring 46 bends toward the connector main body 2 side.

The spring 46 has the stronger restoring force (restoring force to return the movable section 461 back to the original position) to return to the original state in the initial moving period (state shown in FIG. 8) than in the final moving period (state shown in FIG. 9).

For this reason, in this connector 1, when the duct 6 is connected to the connector 1 (upon the connected state), the restoring force of the spring 46 is weak in comparison with the case upon the non-connected state. This feeling is felt by the hand so that it is possible to positively grip with ease the fact that the duct 6 has been connected to the connector 1.

Also, in this connector 1, in comparison with the case of using the biasing means, such as a spiral spring, whose restoring force is increased as it is shrunk and whose restoring force is increased as it is elongated, since it is possible to weaken the restoring force of the spring 46 under the connected state, it is possible to hold the connected state positively by engaging the duct 6 with the proximal end section 31 of the connecting member 3 even if the duct 6 having no lock mechanism is connected to the connector 1.

As described above, according to this connector 1, it is possible to obtain the same effect as that of the connector 1 according to the above-described first embodiment.

Also, in this connector 1, since the spring 46 of the connecting section 4 is located in the interior (inside) of the connecting member 3, there is no fear that anything is brought into direct contact with the spring 46.

It is thus possible to perform the connecting work safely even if the duct 6 having no lock mechanism is to be connected to the connector 1.

Also, since the spring 46 of the connecting section 4 is located in the interior of the connecting member 3, it is possible to take any shape for the outer peripheral shape of the connecting member 3. For instance, it is possible to provide a curved surface or a rib (knurl) or the like corresponding to fingers on the outer peripheral side of the connecting member 3 and to perform with ease a device such as facilitating to grip the connector 1.

Also, in this connector 1, it is possible to connect the valve disc 5 and the connecting member 3 with each other with ease by means of the connecting section 4 without using adhesive technology or the like, thereby making it possible to assemble the connector 1 with ease.

As described above, the connector according to the present invention has been described on the basis of the embodiments. However, the present invention is not limited to these. It is possible to replace each structure to any desired structure having the same function.

For example, according to the present invention, it is possible to combine the above-described embodiments suitably.

Also, according to the present invention, the valve disc 5 is not limited to each of the embodiments. Other structural examples of the valve disc 5 will now be described. Incidentally, for the sake of the explanation, the explanation will be given while regarding the up-and-down direction as an "axial direction", the upper side as a "proximal end" and the lower side as a "distal end" on the paper surface of each sectional view of the valve disc. Also, the common point with the valve disc 5 of the connector 1 according to each embodiment described above will be omitted and only the main differences will be described.

Figure 10A:
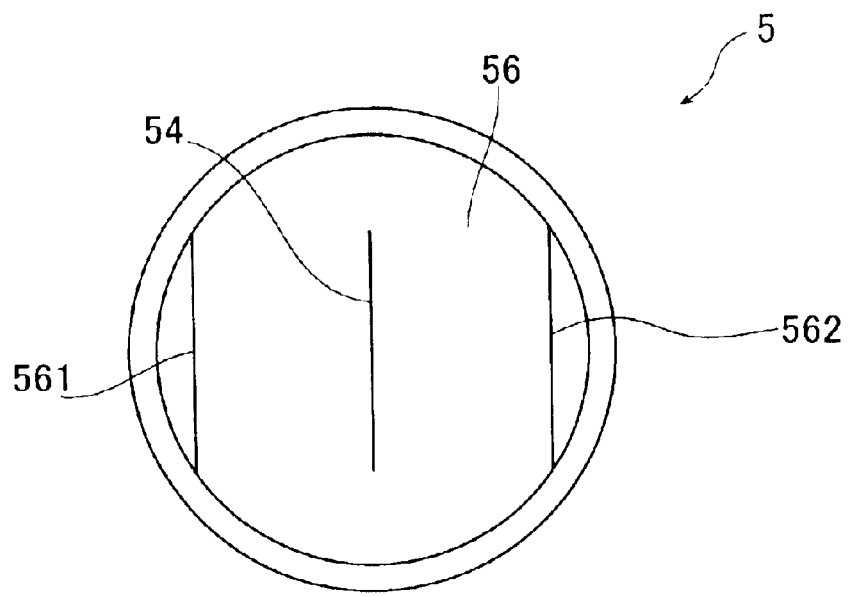
FIGS. 10A and 10B are a plan view and a local sectional view of a side surface showing an structural example of a valve disc according to the present invention.
Figure 10B:
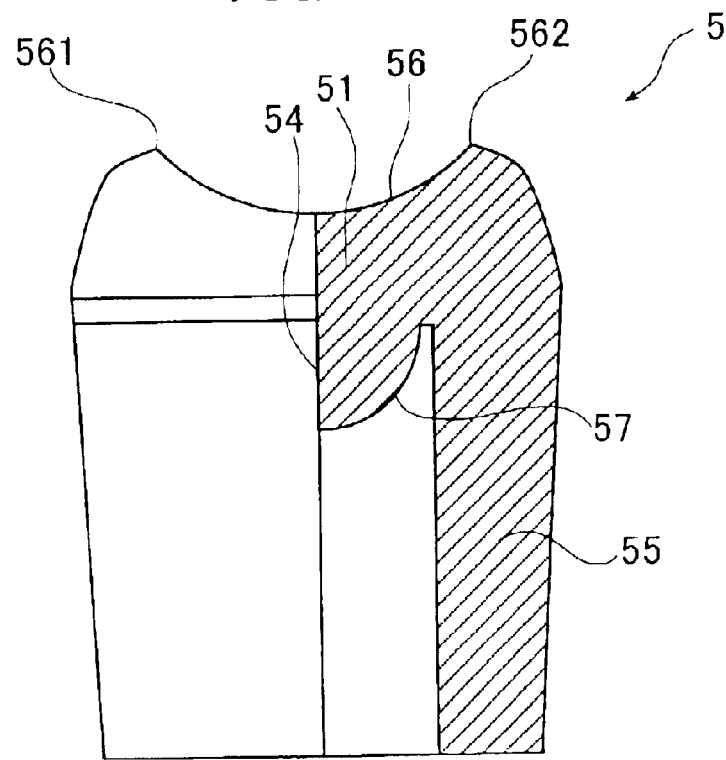
Figure 11A:
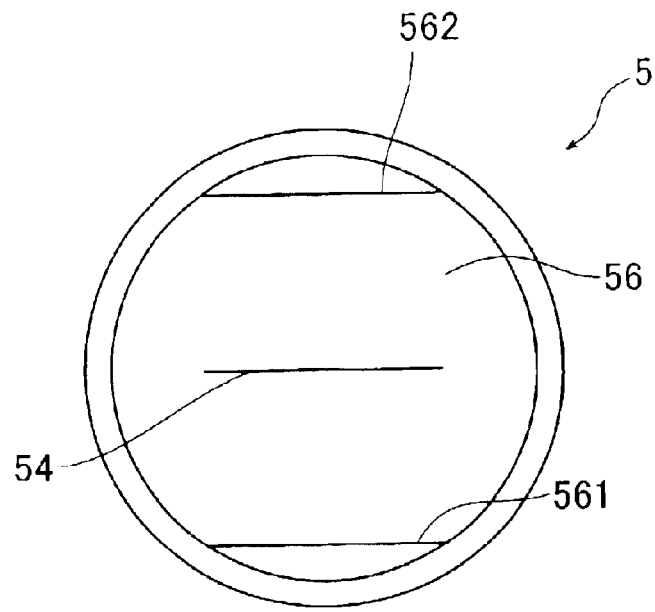
FIGS. 11A and 11B show the valve disc shown in FIG. 10 and are a plan view and a local sectional view of a side surface when the valve disc is turned about its axis by 90 degrees.
Figure 11B:
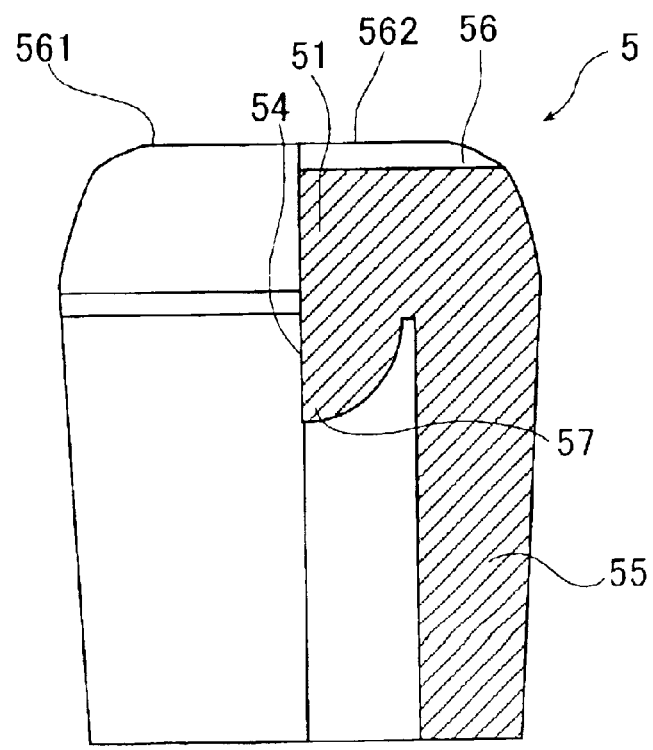
Figure 12:
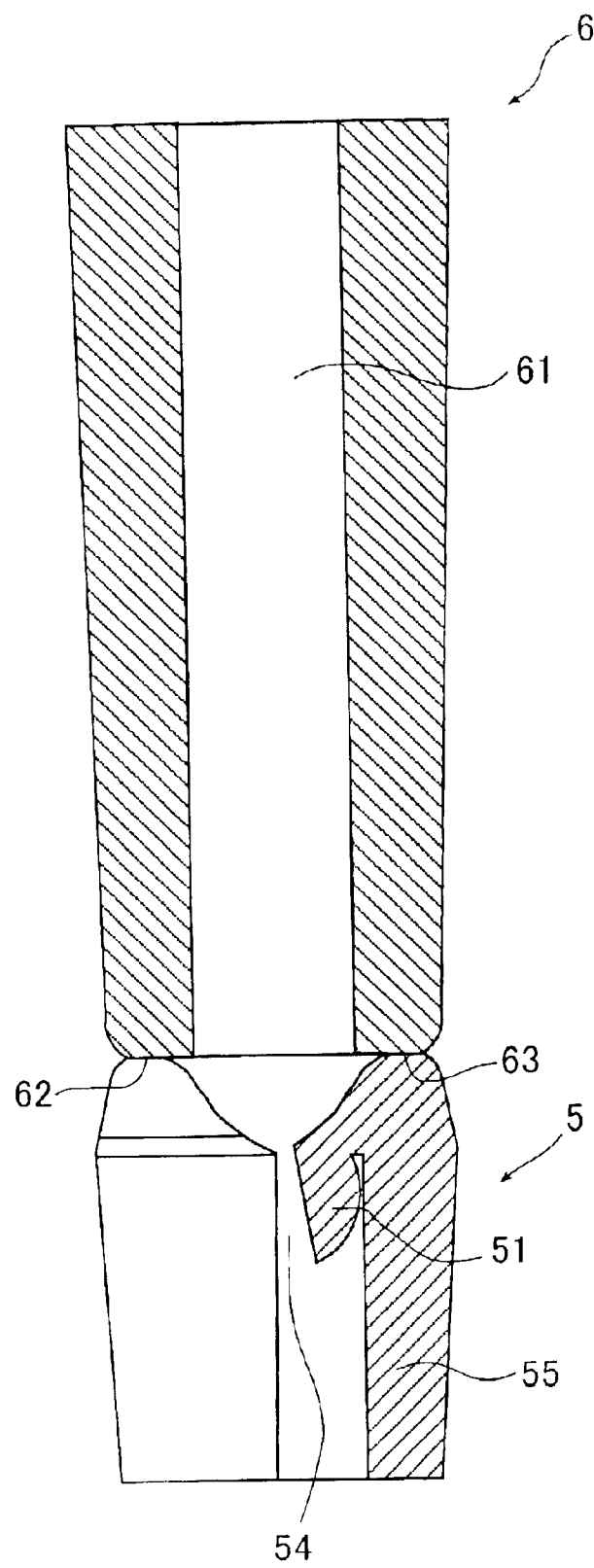
FIG. 12 is a local sectional view of a side surface of the valve disc shown in FIG. 10, which shows a state that a duct is connected.

FIG. 10 corresponds to a plan view showing a structural example of the valve disc 5 (FIG. 10A) and a local sectional view of a side surface (FIG. 10B). FIG. 11 shows the valve disc 5 shown in FIG. 10 and corresponds to a plan view (FIG. 11A) and a local sectional view of a side surface (FIG. 11B) when the valve disc 5 is rotated about its center axis by 90 degrees and FIG. 12 shows the valve disc 5 shown in FIG. 10 and is a local sectional view of a side surface, which shows the state that the duct 6 is connected thereto.

As shown in FIGS. 10 and 11, the pressed section 51 of this valve disc 5 has a curved concave surface 56 on a surface (surface on the proximal end side) on the side with which the distal end surface 62 of the duct 6 is brought into contact and a curved convex surface 57 on a surface (surface on the distal end side) on its back side.

In the plan views shown in FIGS. 10A and 11A, the curved concave surface 56 is curved in a direction perpendicular to the slit section 54 and is not curved in the direction in parallel with the slit section 54.

Namely, the shape of the curved concave surface 56 has a shape such as an inner cylindrical peripheral surface with the axis (center axis) in the up-and-down direction in the plan view shown in FIG. 10A. A pair of linear apex sections 561 and 562 of this curved concave surface 56 are arranged on both sides through the slit section 54 and in parallel with the slit section 54 in the plan view shown in FIGS. 10A and 11A.

Also, the shape of the curved convex surface 57 forms a substantially spherical surface (shape like a hemispherical surface).

As shown in FIG. 12, when the duct 6 is connected to the connector 1, the pressed section 51 of the valve disc 5 is pressed by means of the distal end surface 62 of the duct 6, the slit section 54 is opened at a predetermined opening degree so that the flow path 61 of the duct 6 and the flow path 21 of the connector main body 2 are in communication with each other through this valve disc 5.

In this valve disc 5, since the curved concave surface 56 is formed on the proximal end side of the pressed section 51 as described above, the slit section 54 is likely to be opened when the pressed section 51 is pressed by means of the duct 6. Namely, the slit section 54 is opened largely.

Incidentally, the shape of the curved convex surface 57 may be the shape such as a cylindrical peripheral surface, for example.

Figure 14:
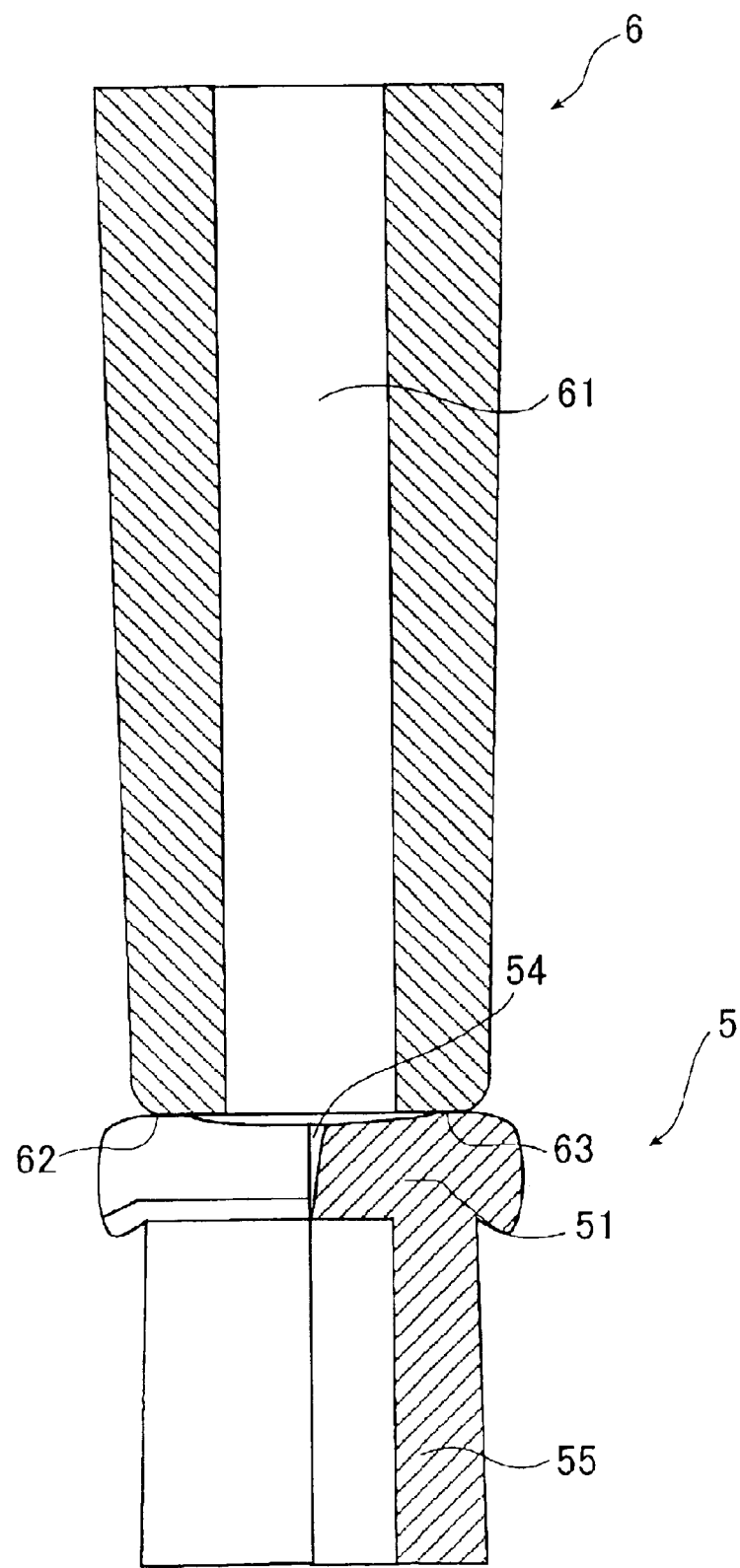
FIG. 14 is a local sectional view of a side surface of the valve disc shown in FIG. 13, which shows a state that a duct is connected.

FIG. 13 corresponds to a plan view (FIG. 13A) showing a structural example of the valve disc 5 and a local sectional view (FIG. 13B) showing its side surface. FIG. 14 shows the valve disc 5 shown in FIG. 13 and is a local sectional view of a side surface, which shows the state that the duct 6 is connected.

As shown in FIG. 13B, the pressed section 51 of this valve disc 5 has the curved concave surface 56 on a surface (surface on the proximal end side) on the side with which the distal end surface 62 of the duct 6 is brought into contact and a surface (surface on the distal end side) on its back side is flat (flat surface 58).

In the plan view shown in FIG. 13A, the curved concave surface 56 is curved in a direction perpendicular to the slit section 54 and is not curved in the direction in parallel with the slit section 54.

Namely, the shape of the curved concave surface 56 has a shape such as an inner cylindrical peripheral surface with the axis (center axis) in the up-and-down direction in the plan view shown in FIG. 13A. The pair of linear apex sections 561 and 562 of this curved concave surface 56 are arranged on both sides through the slit section 54 and in parallel with the slit section 54 in the plan view shown in FIG. 13A.

As shown in FIG. 14, when the duct 6 is connected to the connector 1, the pressed section 51 of the valve disc 5 is pressed by means of the distal end surface 62 of the duct 6, the slit section 54 is opened at a predetermined opening degree so that the flow path 61 of the duct 6 and the flow path 21 of the connector main body 2 are in communication with each other through this valve disc 5.

Figure 15A:
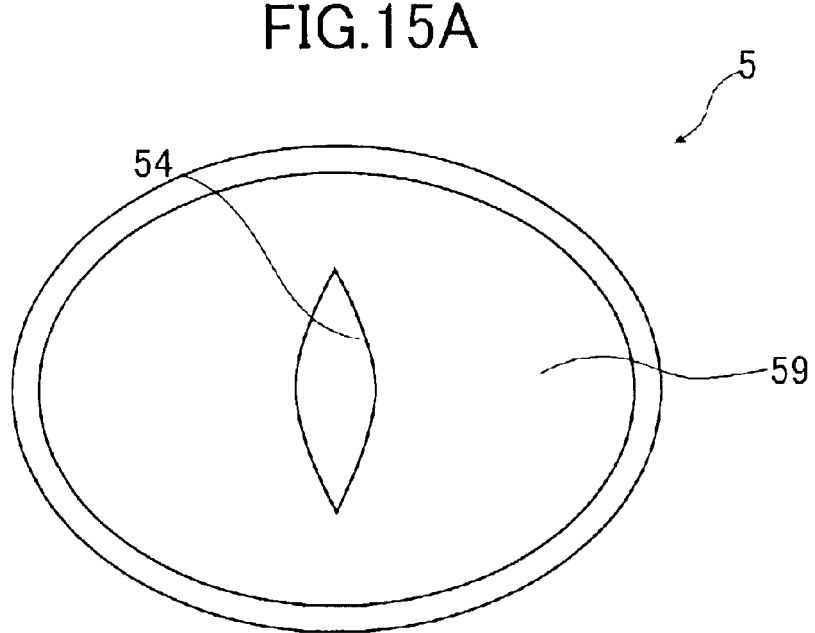
FIGS. 15A and 15B are a plan view and a local sectional view of a side surface showing an structural example of a valve disc according to the present invention.
Figure 15B:
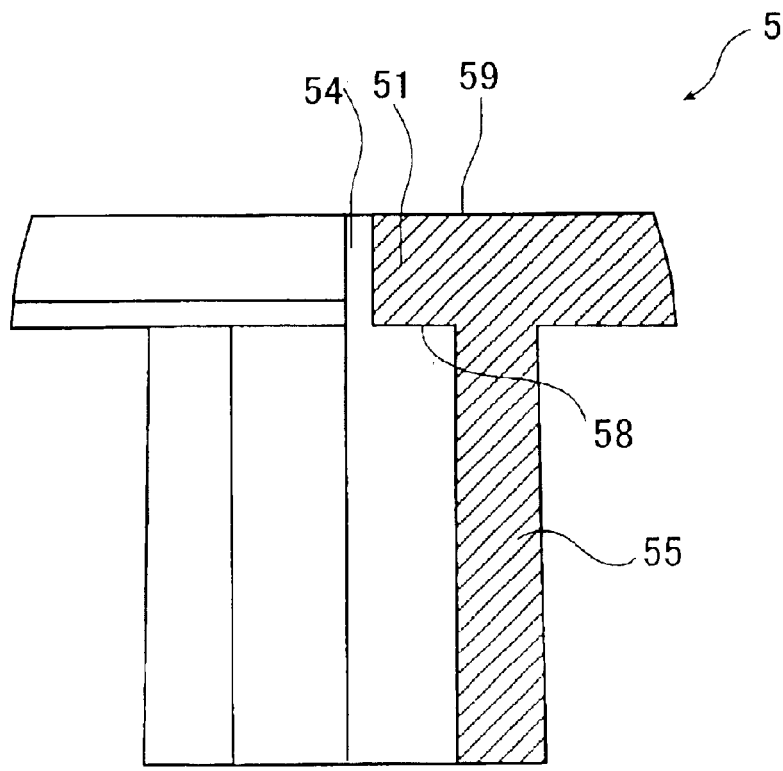
Figure 16A:
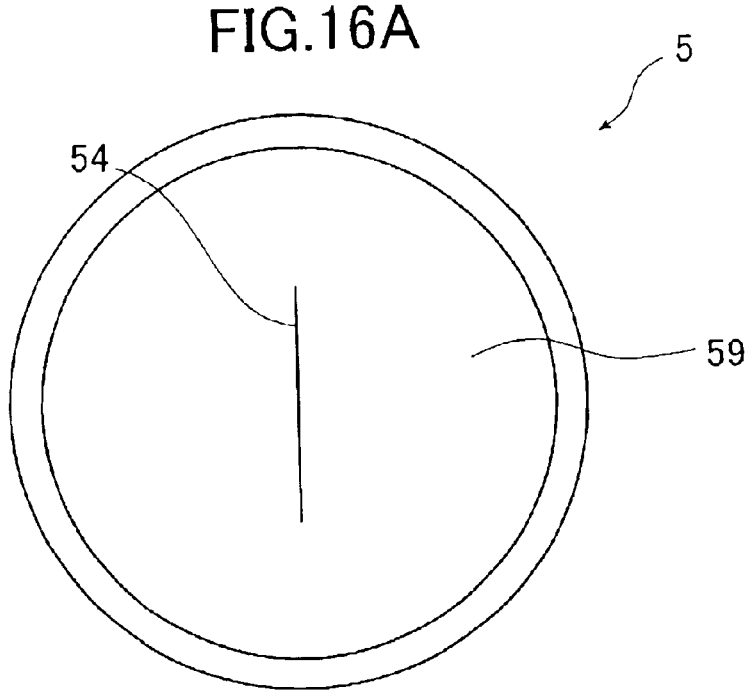
FIGS. 16A and 16B are a plan view and a local sectional view of a side surface of the valve disc shown in FIG. 15, which shows a state that the shape of the valve disc is limited by a connecting member.
Figure 16B:
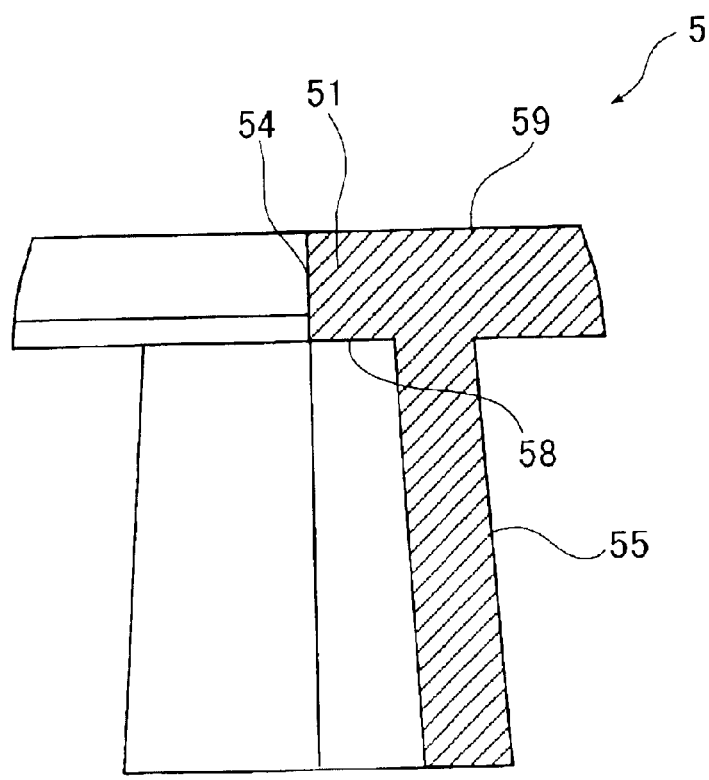

FIG. 15 is a plan view (A) and a local sectional view (FIG. 15B) of a side surface, which shows still another structural example of the valve disc 5. FIG. 16 shows the valve disc 5 shown in FIG. 15 and a plan view (A) and a sectional view (FIG. 16B) of a side surface, which shows the state that the shape of the valve disc 5 is regulated by the connecting member 3.

As shown in FIG. 15, the slit section 54 opened under the natural state is formed in the central section of the pressed section 51 of this valve disc 5. This slit section 54 passes through the pressed section 51.

Here the above-described "natural state" means the non-loaded state in which the external force is not applied to the valve disc 5.

Also, a contour (contour shape) in a plan view of the pressed section 51, i.e., a contour of the pressed section 51 when the pressed section 51 is projected onto the plan view perpendicular to the axial direction forms an oblong shape (non-circular shape) under the natural state.

Also, the surface (surface on the proximal end side) of the side with which the distal end surface 62 of the duct 6 contacts and the surface (surface on the distal end side) on the back side thereof of the pressed section 51 are each flat (flat surfaces 59 and 58).

When the connector 1 provided with this valve disc 5 is assembled (the valve disc 5 is mounted on the connector 1) and the duct 6 is not connected to the connector 1 (upon the non-connected state), the valve disc 5 is located at the proximal end section 31 of the connecting member 3 (see FIG. 1) and the shape of the valve disc 5 is regulated by this proximal end section 31.

Thus, as shown in FIG. 16, the contour of the plan view of the pressed section 51 is formed into a substantially circular shape (the same shape as the inner shape of the proximal end section 31) and the slit section 54 is closed.

Then, when the duct 6 is connected to the connector 1, the valve disc 5 is located at the distal end section 32 of the connecting member 3 (see FIG. 2). Namely, the regulation of the shape of the valve disc 5 by the proximal end section 31 is released.

Thus, as shown in FIG. 15, the contour in the plan view of the pressed section 51 is returned back to the original shape, i.e., the oblong shape (non-circular shape), and the slit section 54 is opened so that the flow path 61 of the duct 6 and the flow path 21 of the connector main body 2 are in communication with each other through this valve disc 5.

Also, according to the present invention, the valve disc 5 may be formed of elastic material of two different kinds of materials in composition or characteristics (flexibility, bending elastic rate, rubber hardness or the like).

Also, in the above-described embodiments, the shape of the slit of the slit section 54 is formed into the straight-line or the cross-shaped. However, according to the present invention, the shape is not limited to those but may be formed into, for example an L-shape, an H-shape, a U-shape or the like. Furthermore, at the time when the flow rate of the fluid has to be increased or decreased in accordance with the use, and so on, a plurality of slits may be formed in the slit section 54.

Figure 17:
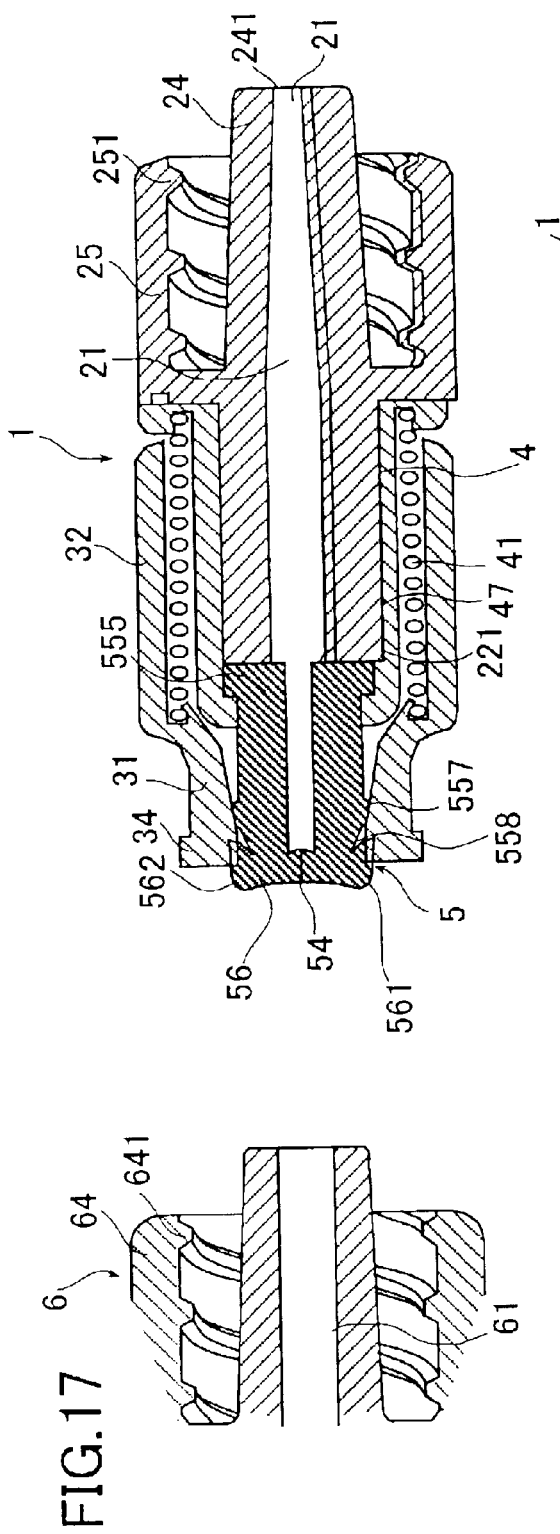
FIG. 17 is a side sectional view in accordance with a fifth embodiment of a connector of the present invention, which shows a state that a duct is not connected.
Figure 18:
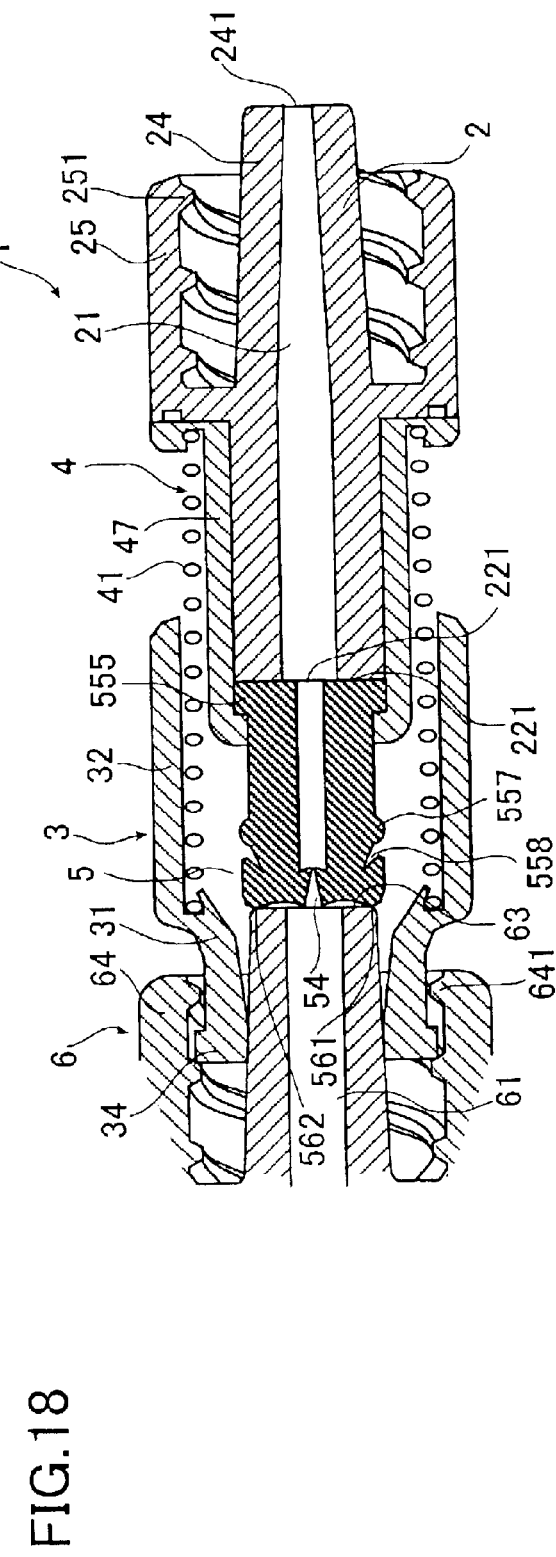
FIG. 18 is a side sectional view in accordance with the fifth embodiment of the connector of the present invention, which shows a state that the duct is connected.

A fifth embodiment is shown in FIGS. 17 and 18 as still another mode of a connector according to the present invention.

FIG. 17 is a side sectional view showing a state that the connector 1 and the duct 6 are not connected to each other, and FIG. 18 is a side sectional view showing the state that the duct 6 is connected to the connector 1.

According to this mode, the duct 6 has a lure lock 64 provided with a spiral rib (lure lock screw) 251 on an inner periphery on a tip end section of the duct. The duct distal end surface 62 is projected by a predetermined length from a tip end of a section of the lure lock 25.

Upon the connected state (FIG. 17), the duct 6 is not only connected and fit to the opening 311 of the connecting member 3 but also it is fixed by means of the engagement between the lure lock 64 of the duct 6 and the connecting member 3 (flange 34) of the connector 1.

The connecting member 3 has the flange 34 and the long taper surface 331 in the stepped section 33.

The valve disc 5 has the pair of apexes 561 and 562 having the distal end surface 62 formed into the curved concave surface 56 substantially in the same manner as in FIG. 10B in a side sectional view in the vicinity of the pressed section 51 and the curved convex surface 57 on its back surface. The rib 555 is provided at a tip end of the base body section 55 of the valve disc 5. Furthermore, a convex retainer section 557 is provided on an outer periphery of the base body section 55. A notch 558 that may be bent upon depression from the distal end section is provided on a side wall of the base end side from the retainer section 557.

The slit 54 has a wedge-shaped opening that has the flow path 21 side of the connector main body narrowed in diameter by the bending of the notch 558 due to the depression from the distal end section.

The connecting section 4 is composed of a spiral spring (biasing means) 41 and a cylindrical attaching section 47 arranged around an axial outer periphery from the distal end of the connector main body 2 to the distal end side in which the lure lock is formed. The number of windings of this spring 41 may be higher than that of the spring shown in FIG. 1. The attaching section 47 fixes one end of the spring 41 by a groove 471 formed on its distal end side and fixes the rib 555 of the valve disc 5 to the connector main body 2 by a retainer 472 formed at the other end on the proximal end side. Thus, the valve disc 5 is positively fixed to the connector main body 2. Also, since the connecting member 3 is slid through a long stroke along the attaching section 47 along a barrel section of the connector main body 2 upon the connection with the duct 6, it is possible to perform the connection smoothly and stably.

Also, the valve disc 5 is held in a predetermined position by the retention of the valve disc 5 to the proximal end side wall by the opening 311 of the connecting member 3 and the retention of the convex retainer section 557 to the taper surface 331 of the connecting member 3.

FIGS. 19 and 20 show a sixth embodiment of a connector according to the present invention. FIG. 19 is a side sectional view showing a state that the connector 1 and the duct 6 are not connected to each other, and FIG. 20 is a side sectional view showing the state that the duct 6 is connected to the connector 1.

In the drawing, the valve disc 5 shows a modified mode of the valve disc 5 and the connecting section 4 shown in FIG. 4 and the function of the stepped spring 461 in FIG. 4 is given to the valve disc 5.

The connector main body 2 has a valve insertion barrel section 26 having a smaller outer diameter on the proximal end side of the proximal end section 22 and the flow path 21 is somewhat expanded on the proximal end surface of the barrel section 26. According to this mode, the base body section 55 of the valve disc 5 has a shape to cover the proximal end section 22 including the barrel section 26 of the connector main body 2 and a wing 559 that extends in a double tube shape outwardly from the tip end rib 555 of the base body section 55. The tip end section 560 of the wing 559 is pressed and fixed to the intermediate vicinity to the base body section 55 by a proximal end 48 of the connecting section 4 and the tip end section 32 of the connecting member 4 (in the non-connected state).

A part of the base body section outer periphery of the valve disc 5 is fixed to the connector main body 2 by the ring-like retainer 49.

Upon the connection (FIG. 20), when the lure lock 64 of the duct 6 and the connecting member 3 (flange 34) of the connector 1 are engaged with each other, and the outer periphery of the duct 6 is fit in the opening 311 of the connecting member 3, the wing 559 of the valve disc 5 extends from the vicinity of the ring-like retainer 49 to the proximal end side to follow the movement of the connecting member 3.

FIG. 21 shows still another mode of a connector according to the present invention and an example in which a plurality of connectors 1 are arranged in parallel. FIG. 21 shows an example in which three connectors are arranged in parallel. Each connector 2 has the same structure with the same arrangement as that of each of the valve disc 5, the connecting member 3 and the connecting section 4 shown in FIGS. 19 and 20.

The connecting pipe 7 has a flow path 72 in the interior and has a plurality of openings 73 in the body side wall 72 thereof. According to the mode shown in FIG. 21, the connector main body 2 is composed by making one the tip end opening 241 of each connector main body 2 and each opening 73 of the connecting pipe 7 to be continuous with the body side wall 71 of the connecting pipe 7 and to be formed integrally preferably.

In such a connecting pipe, it is possible to introduce a plurality of kinds of liquids by a single catheter by providing a plurality of connectors used in, for example, a universal plug, a syringe, an infusion container, a medicine liquid container, a catheter, a needle or the like to thereby make it possible to reduce the load to be imposed on the patient.

INDUSTRIAL APPLICABILITY

As described above, in the connector according to the present invention, since the volume of the flow path does not substantially vary before and after the connection of the duct, when the duct is detached from and attached to the connector, it is possible to prevent the fluid (liquid, gas or the like) from being accidentally sucked or discharged.

For instance, in the case where the connector is connected to the catheter disposed in the blood vessel and used, even if the duct is removed from the connector, there is no fear that the blood is sucked into the catheter to thereby make it possible to prevent (or suppress) the generation of thrombi within the catheter.

What is claimed is:

1. A connector comprising: a substantially cylindrical connector main body having a flow path in its interior and opened at both ends; a valve disc disposed at one of opening ends of said connector main body and made of elastic material for opening said fluid passage within the connector main body upon the connection with a duct to be connected to the connector main body and closing upon the non-connection; and a substantially cylindrical connecting member disposed on the outer periphery of said connector main body on a side of said valve disc and coaxially with the connector main body to be movable in an axial direction of the connector main body.

2. A connector according to claim 1, wherein said valve disc is opened by a pressure from said duct without said duct passing through the interior of the valve disc.

3. A connector according to claim 1, wherein said duct is fit to an opening of said connecting member to thereby connect and hold the duct.

4. A connector according to claim 1, further comprising biasing means for biasing said connecting member toward said connector main body.

5. A connector according to claim 4, wherein said biasing means is composed of a spiral spring, a bellows spring or a stepwise spring.

6. A connector according to claim 1, further comprising position regulating means for regulating a position of said connecting member so as to expose a part of said valve disc in the vicinity of said connecting port at the time when said duct is not connected to said connecting port.

7. A connector according to claim 1, wherein said valve disc has a pressed section in which a slit section that is opened due to reception of the pressure from said duct is formed.

8. A connector according to claim 7, wherein said pressed section has a curved convex surface on at least one of a surface on a side with which a distal end surface of said duct contacts and a surface on its back side.

9. A connector according to claim 7, wherein said pressed section has a curved concave surface on a surface on a side with which a distal end surface of said duct contacts.

10. A connector according to claim 9, wherein said pressed section has a curved convex surface on the surface on the back side on the side with which the distal end surface of said duct contacts.

11. A connector according to claim 7, wherein the surface on the back side on the side, with which the distal end surface of said duct contacts, of said pressed section is flat.

12. A connector according to claim 7, wherein said pressed section has a flat surface on the side with which the distal end surface of said duct contacts.

13. A connector according to claim 7, wherein said pressed section has a first convex section on the side with which the distal end surface of said duct contacts.

14. A connector according to claim 13, wherein said first convex section is formed into a substantially dome shape.

15. A connector according to claim 13, wherein said pressed section has a second convex section projecting opposite the first convex section on the back side of said first convex section.

16. A connector according to claim 15, wherein said second convex section is formed into a substantially hemispherical shape.

17. A connector according to claim 1, wherein said valve disc has a pressed section provided with a slit section opened upon the natural state and the shape of said valve disc is regulated by said connecting member upon the non-connection between said duct and said connector main body so that said slit section is closed.

18. A connector according to claim 17, wherein a contour in plan view of said pressed section has a non-circular shape upon the natural state, and the shape of said valve disc is regulated by means of said connecting member to become substantially circular.

19. A connector according to claim 1, wherein the fluid passage distance of said connector main body defined between the contact surface between said duct and said valve disc disposed at one end of said connector main body and an opening on the other end does not substantially vary with the opening/closing of the valve disc before and after the connection between said duct and said connector main body.

20. A connector according to claim 1, wherein the volume of said fluid passage of said connector main body does not substantially vary before and after the connection between said duct and said connector main body.

* * * * *

UNITED STATES PATENT AND TRADEMARK OFFICE
CERTIFICATE OF CORRECTION

PATENT NO. : 6,811,139 B2
DATED : November 2, 2004
INVENTOR(S) : Yoshinori Hishikawa It is certified that error appears in the above-identified patent and that said Letters Patent is hereby corrected as shown below:

<u>Title page,</u>
Item [87], PCT Pub. Date, change "May 21, 2001" to -- June 21, 2001 --.

Signed and Sealed this

Eleventh Day of October, 2005

JON W. DUDAS
*Director of the United States Patent and Trademark Office*